US012735460B2

(12) United States Patent
Wu et al.

(10) Patent No.: US 12,735,460 B2
(45) Date of Patent: Sep. 15, 2026

(54) METHOD FOR PREPARING AND CERTIFYING NOVEL CORONAVIRUS NUCLEOCAPSID PROTEIN

(71) Applicant: NATIONAL INSTITUTE OF METROLOGY, CHINA, Beijing (CN)

(72) Inventors: Liqing Wu, Beijing (CN); Xinhua Dai, Beijing (CN); Wei Mi, Beijing (CN); Yahui Liu, Beijing (CN); Tao Peng, Beijing (CN); Jie Xie, Beijing (CN)

(73) Assignee: NATIONAL INSTITUTE OF METROLOGY, CHINA, Beijing (CN)

( * ) Notice: Subject to any disclaimer, the term of this patent is extended or adjusted under 35 U.S.C. 154(b) by 460 days.

(21) Appl. No.: 18/518,834

(22) Filed: Nov. 24, 2023

(65) Prior Publication Data

US 2024/0199707 A1 Jun. 20, 2024

Related U.S. Application Data

(63) Continuation of application No. PCT/CN2023/078589, filed on Feb. 28, 2023.

(30) Foreign Application Priority Data

Mar. 9, 2022 (CN) ......................... 202210245575.4

(51) Int. Cl.

| | |
|---|---|
| ***C07K 14/165*** | (2006.01) |
| ***C07K 1/14*** | (2006.01) |
| ***C07K 1/18*** | (2006.01) |
| ***C07K 1/28*** | (2006.01) |
| ***C07K 1/36*** | (2006.01) |

(52) U.S. Cl.

CPC .............. *C07K 14/165* (2013.01); *C07K 1/18* (2013.01); *C07K 1/28* (2013.01); *C07K 1/36* (2013.01)

(58) Field of Classification Search

CPC .......... C07K 14/165; C07K 1/18; C07K 1/28; C07K 1/36; C07K 14/005; Y02A 50/30; G01N 27/447; G01N 27/64; G01N 30/02; G01N 30/32; G01N 30/34; G01N 30/72; G01N 30/74; G01N 33/68; G01N 33/6848; G01N 2030/324; C12N 2770/20022

See application file for complete search history.

(56) References Cited

U.S. PATENT DOCUMENTS

| | | | | |
|---|---|---|---|---|
| 2007/0275002 A1* | 11/2007 | Van Der Werf | ........ | A61P 11/06 435/243 |
| 2017/0253908 A1* | 9/2017 | Eichmeyer | ....... | G01N 33/56983 |
| 2022/0023415 A1* | 1/2022 | King | ...................... | A61K 39/12 |

FOREIGN PATENT DOCUMENTS

| | | | | |
|---|---|---|---|---|
| CN | 108614104 A | | 10/2018 | |
| CN | 111308072 A | | 6/2020 | |
| CN | 112505330 A | | 3/2021 | |
| CN | 112763628 A | * | 5/2021 | ............. G01N 30/02 |
| CN | 114702555 A | | 7/2022 | |
| WO | WO-2019066389 A1 | | 4/2019 | |

OTHER PUBLICATIONS

PCT/CN2023/078589, Written Opinion of the International Searching Authority (English Translation). Filed Feb. 28, 2023. (Year: 2023).*

International Search Report of PCT/CN2023/078589, Jun. 16, 2023, 4 pages.

First search report of prior CN application No. 202210245575.4, Aug. 17, 2022, 2 pages.

* cited by examiner

*Primary Examiner* — Brian J. Sines

(74) *Attorney, Agent, or Firm* — MUNCY, GEISSLER, OLDS & LOWE, P.C.

(57) ABSTRACT

Disclosed in the present invention is a method for preparing and certifying a novel coronavirus nucleocapsid protein (nCOV N protein) reference material, the method including: purification and dilution of a raw material of the nCOV N protein; preliminary uniformity test and packaging of solution of a candidate nCOV N protein reference material; characterization of physicochemical properties of the solution of the candidate nCOV N protein reference material in the packaging units; uniformity and stability test of the nCOV N protein reference material in the packaging unit; measurement of standard N protein content of the nCOV N protein reference material, determination and statistical test of standard value of the nCOV N protein reference material; and uncertainty assessment of certified result of the standard value of the nCOV N protein reference material.

8 Claims, No Drawings

Specification includes a Sequence Listing.

METHOD FOR PREPARING AND CERTIFYING NOVEL CORONAVIRUS NUCLEOCAPSID PROTEIN

REFERENCE TO AN ELECTRONIC SEQUENCE LISTING

The content of the electronic sequence listing (2024-03-08-Sequence-Listing.xml; Size: 23,919 bytes; and Date of Creation: Mar. 8, 2024) is herein incorporated by reference in its entirety.

TECHNICAL FIELD

The present invention relates to the technical field of stoichiometric chemical analysis and detection, in particular to a preparation and certification technology of a novel coronavirus nucleocapsid protein (nCOV N protein) reference material.

BACKGROUND

Since December 2019, a sudden plague has swept across the globe. The chief culprit causing the plague is a highly infective novel coronavirus (2019-nCOV). At that time, confirmed and suspected cases increased rapidly, and epidemic prevention and control has become a top priority for whole country. The diagnosis of Corona Virus Disease 2019 (COVID-19) patients depends on the results of clinical testing, and the accuracy of the results of the clinical testing is directly associated with the success or failure of fighting the outbreak. For clinic testing, the clinical testing of COVID-19 patients mainly relies on methods of molecular biology and immunology. The coronavirus N protein is an important structural protein of 2019-nCOV, which plays a key role in the processes of packaging, replication of virus and protein translation, etc. N protein is a nucleocapsid phosphoprotein with a highly conserved gene sequence FYYLGTGP at its N-terminus. N protein first combines with a genomic RNA in cytoplasm to form a spirally coiled nucleocapsid, and then interacts with M- and E-proteins to wrap it into the virus capsid. S-protein is inserted when a budding from the virus membrane becomes mature, and interacts with M-protein to form a virion which is released from the vesicle. There are two mutual recognitions between the N protein and the viral genomic RNA, one is that the N protein can only be combined with a complete viral genomic RNA, which is associated with the packaging signal sequence in the viral genomic RN; and the other is that the M-protein interacts with a conjugate of the N protein and the viral RNA, which is associated with some co-factors. The viral N protein can be detected 1-2 days after the patient is infected, and thus the purpose of "early detection, early isolation, and early treatment" can be achieved, which has a positive significance for prevention and control of outbreak.

Certification is an activity to achieve the unity of units and the accuracy and reliability of values, and the accurate and comparable measurement results are achieved through the traceability of values using a reference material. The accuracy of the pure N protein substance, serving as the primary source of values, directly determines the reliability of the test results. To ensure the accuracy and comparability of the test results of the N protein, it is required to develop a nCOV N protein reference material, which can be used as a carrier for value transfer and used as a calibration standard during the determination of N protein or in the confirmation and verification of a method.

SUMMARY OF THE INVENTION

An inventive object of the present application is to provide a method for preparing and certifying a novel coronavirus nucleocapsid protein (nCOV N protein) reference material, which is intended to fill in the gap of the related technology and ensure the accuracy and effectiveness of the test results of the nCOV N protein.

To achieve the inventive object of the present application, the present application utilizes the following technical solutions:

A method for preparing and certifying a novel coronavirus nucleocapsid protein (nCOV N protein) of the present invention includes the following steps:

(I). Purification and Dilution of a Raw Material of the nCOV N Protein (a) purification of the raw material of the nCOV N protein the nCOV N protein is an N protein sequence of SEQ ID NO: 1 as set forth below, or a protein sequence with (3 to 10) histidine or lysine attached to one or both ends of the N protein sequence of SEQ ID NO: 1:

```
  1 MSDNGPQNQR NAPRITFGGP SDSTGSNQNG ERSGARSKQR RPQGLPNNTA SWFTALTQHG KEDLKFRPGQ GVPINTNSSP

 91 DDQIGYYRRA TRRIRGGDGK MKDLSPRWYG YYLGTGPEAG LPYGANKDGI IWVATEGALN TPKDHIGTRN PANNAAIVLQ

161 LPQGTTLPKG FYAEGSRGGS QASSRSSSRS RNSSRNSTPG SSRGTSPARM AGNGGDAALA LLLLDRLNQL ESKMSGKGQQ

241 QQGQTVTKKS AAEASKKPRQ KRTATKAYNV TQAFGRRGPE QTQGNFGDQE LIRQGTDYKH WPQIAQFAPS ASAFFGMSRI

321 GMEVTPSGTW LTYFGAIKLD DKDPNFKDQV ILLNKHIDAY KTFPPTEPKK DKKKKADETQ ALPQRQKKQQ TVTLLPAADL

401 KKFSKQLQQS NSSADSTQA
```

the raw material is from a commercially available nCOV N protein biochemical reagent with a purity of 90% to 95%, for obtaining a candidate nCOV N protein reference material with a high purity, the biochemical reagent is purified by an isoelectric focusing method and/or a molecular sieve method to give the candidate nCOV N protein reference material with a purity of 98.5% or above;

(b) preliminary measurement of concentration of the candidate nCOV N protein reference material $^{13}C$ isotope-labeled valine and phenylalanine with a concentration of (0.001 to 1) mg/ml are added into to (1~100) μL of the candidate nCOV N protein reference material, the mixture is subject to centrifugal concentration or nitrogen blowing, and then (100 to 1000) μL of concentrated hydrochloric acid with a concentration of (6 to 8) mol/L is added thereto, and sealed while passing nitrogen for protection, the mixture is hydrolyzed in an oven at 110° C. to 150° C. for 24 to 72 hours to give a hydrolysate, and after hydrolysis, an amino acid content in the hydrolysate is measured by performance liquid chromatography-isotopic dilution mass spectrometry (HPLC-IDMS) using national reference materials of valine and phenylalanine as standard, and an initial concentration of the candidate nCOV N protein reference material is calculated according to the N protein sequence of SEQ ID NO: 1;

(c) dilution of the candidate nCOV N protein reference material the candidate nCOV N protein reference material, of which the concentration has been preliminarily measured, is diluted with PBS as solvent to a concentration ranging from (0.05 to 0.2) mg/g to give a diluted solution of the candidate nCOV N protein reference material;

(II). Preliminary Uniformity Test and Packaging of the Solution of the Candidate nCOV N Protein Reference Material (d) preliminary uniformity test of the solution of the candidate nCOV N protein reference material 3 sub-samples are taken from each of upper, middle, and lower parts of the diluted solution of the candidate nCOV N protein reference material in step (c), respectively, to obtain a total of 9 test samples, the 9 test samples are numbered and arranged in order, and the content of the nCOV N protein in each test sample is subject to a first test by isotopic dilution mass spectrometry (IDMS), amino acid analysis (AAA), or immunoassay, then the order is disrupted, and the content of the nCOV N protein in each test sample is subject to a second test, the above operations are repeated until each test sample is tested three times, obtaining 27 test results, and the uniformity of content $\overline{x}$ of the nCOV N protein in the taken test sample is calculated according to the formulas below;

when m=9 samples are taken, 9 sets of precisely measured data are obtained according to the above test method under a condition of repeatability n=3, as shown below:

No. 1: $x_{11}, x_{12} \ldots x_{1n}$, with a mean value of $\overline{x}_1$

No. 2: $x_{21}, x_{22} \ldots x_{2n}$, with a mean value of $\overline{x}_2$

. . .

No. m: $x_{m1}, x_{m2} \ldots x_{mn}$, with a mean value as below:

$$\text{mean value} = x = \frac{\sum_{i=1}^{m} \overline{x_i}}{m} \quad \text{Formula (1)}$$

$$\text{statistical value } N \quad N = m \cdot n \quad \text{Formula (2)}$$

sum of squares of between-group differences:

$$Q_1 = \sum_{i=1}^{m} n\left(\overline{x_i} - \overline{\overline{x}}\right)^2 \quad \text{Formula (3)}$$

sum of squares of intra-group differences:

$$Q_2 = \sum_{i=1}^{m}\sum_{j=1}^{n} (x_{ij} - \overline{x_i})^2 \quad \text{Formula (4)}$$

degree of freedom between groups: $v_1$=m−1; degree of freedom within groups:

$$v_2 N - m$$

$$S_1^2 = \frac{Q_1}{v_1} \quad \text{Formula (5)}$$

$$S_2^2 = \frac{Q_2}{v_2} \quad \text{Formula (6)}$$

statistical value F:

$$F = \frac{S_1^2}{S_2^2} \quad \text{Formula (7)}$$

wherein, $S_1^2$ is variance between groups, $S_2^2$ is variance within groups, according to degree of freedom, $v_1$, $v_2$, and a given significance level of $\alpha$=0.05, a critical value of $F_{\alpha,(v_1,v_2)}$ is obtained by table look-up, and an F value calculated from Formula 7 is compared with $F_\alpha$, if $F<F_\alpha$, it is considered that there is no significant difference between within-groups and between-groups, and the nCOV N protein in the taken test sample is uniform; otherwise, the content of the nCOV N protein in the taken test sample is not uniform, and if the content of the nCOV N protein in the taken test sample is not uniform, the steps (a) to (c) are repeated until the solution of the candidate nCOV N protein reference material in the taken test sample passes the preliminary uniformity test;

(e) packaging of the solution of the candidate nCOV N protein reference material the solution of the candidate nCOV N protein reference material passing the preliminary uniformity test of step (d) is packaged into silanized cryotubes with volume of (500 μL to 2 mL) with (10 μL to 500 μL) of the candidate solution in each silanized cryotube, the packaged solution of the candidate nCOV N protein reference material is labeled and consecutively numbered according to the packaging order to obtain a total of P packaging units, which are then stored in a refrigerator at −80° C.;

(III). Characterization of Physicochemical Properties of the Solution of the Candidate nCOV N Protein Reference Material in the Packaging Unit (f) purity test of the nCOV N protein reference material in the packaging unit the purity of the nCOV N protein reference material in the packaging unit is characterized by a universal protein purity analysis method;

(g) characterization of molecular weight of the nCOV N protein reference material in the packaging unit a molecular weight of the nCOV N protein reference material in the packaging unit is determined by gel electrophoresis, and/or gel exclusion HPLC, and/or mass spectrometry, and the mean value of the determination results should be consistent with theoretical molecular weight of the N protein sequence of SEQ ID NO: 1;

(h) protein identification of the nCOV N protein reference material in the packaging unit the nCOV N protein is digested with trypsin and/or V8 protease, the peptide fragments generated from the protease digestion are identified by peptide mass fingerprinting or tandem mass spectrometry, and then a target protein is obtained by searching the SWISSPROT database through SQEUEST or MASCOT, and the result should be consistent with the protein corresponding to the N protein sequence of SEQ ID NO:1;

(i) de novo sequencing of the nCOV N protein reference material in the packaging unit the nCOV N protein is digested with trypsin and/or V8 protease, and the digested peptide fragments are subject to de novo sequencing by HPLC-tandem mass spectrometry; and amino acid sequence of the peptide fragment is determined by b, y ion series generated from each peptide fragment; amino acid sequences of all the obtained peptide fragments are spliced manually or by a random matching software or a third-party software to give a full-length sequence of the nCOV N protein which should be consistent with the protein sequence corresponding to the N protein of SEQ ID NO: 1;

or the nCOV N protein is digested with trypsin and/or V8 protease, the digested peptide fragments are isolated by reverse phase HPLC, all the peptide fragments with good isolation degree and correspondingly high peak signals are collected one by one, lyophilized, reconstituted in water containing 0.1% formic acid, and then spotted on a PVDF membrane, each collected peptide fragment is subject to de novo sequencing with a protein sequencer based on the Edman principle, sequences of all the peptide fragments are spliced to obtain a full-length sequence of the nCOV N protein, and the result should be consistent with the protein sequence corresponding to the N protein sequence of SEQ ID NO: 1;

(j) identification and certification of impurity proteins in the nCOV N protein reference material in the packaging unit in the purity test of the nCOV N protein reference material in step (f), if an individual impurity has a content exceeding 1%, a fraction containing the impurity is collected out and identified according to steps (f) to (h) for impurity protein; after identification, the impurity is purchased or expressed by recombination to made a standard of the impurity, and then a standard curve is plotted, with horizontal axis representing a concentration of the standard and vertical axis representing a corresponding signal; otherwise, it is not required to identify and certify the impurity;

(IV). Uniformity and Stability Test of the nCOV N Protein Reference Material in the Packaging Unit (k) uniformity test of the nCOV N protein reference material in the packaging unit the consecutively numbered packaging units are randomly sampled with a randbetween function in Excel, when P≤200, the number m of the sampled packaging units is not less than 11; when 200<P≤500, the number m of the sampled packaging units is not less than 15; when 500<P≤1000, the number m of the sampled packaging units is not less than 25; when the packaging units P>1000, the number m of the sampled packaging units is not less than 30; according to the sampling order, the m sampled packaging units are re-numbered and arranged in order, the N protein content of the nCOV N protein reference material in the sampled packaging unit is subject to a uniformity test by IDMS, or amino acid analysis, or immunoassay; during the test, the N protein in the nCOV N protein reference material in each sampled packaging unit is subject to a first test according to the above order, and then the order is disrupted, and the N protein content in the nCOV N protein reference material in each sampled packaging unit is subject to a second test, the above operations are repeated until the N protein in the nCOV N protein reference material in each sampled packaging unit is subject to a $n^{th}$ test, wherein n is an integer greater than or equal to 3, to give n test results, and an uniformity of the N protein in the nCOV N protein reference material in the packaging units are calculated and counted out according to the formulas below;

when m samples are taken, m sets of precisely measured data are obtained according to the above test method under a condition of repeatability n, as shown below:

No. 1: $x_{11}, x_{12} \ldots x_{1n}$, with a mean value of $\overline{x}_1$

No. 2: $x_{21}, x_{22} \ldots x_{2n}$, with a mean value of $\overline{x}_2$

. . .

No. m: $x_{m1}, x_{m2} \ldots x_{mn}$, with a mean value of $\overline{x}_m$:

$$\text{mean value} = x = \frac{\sum_{i=1}^{m} \overline{x_i}}{m} \qquad \text{Formula (8)}$$

statistical value N $$N = m \cdot n \qquad \text{Formula (9)}$$

sum of squares of between-group differences:

$$Q_1 = \sum_{i=1}^{m} n(\overline{x_i} - \overline{\overline{x}})^2 \qquad \text{Formula (10)}$$

sum of squares of intra-group differences:

$$Q_2 = \sum_{i=1}^{m} \sum_{j=1}^{n} (x_{ij} - \overline{x}_i)^2 \qquad \text{Formula (11)}$$

degree of freedom between groups: $v_1$=m−1; degree of freedom within groups:

$$v_2 = N - m$$

$$S_1^2 = \frac{Q_1}{v_1} \qquad \text{Formula (12)}$$

$$S_2^2 = \frac{Q_2}{v_2} \qquad \text{Formula (13)}$$

statistical value F:

$$F = \frac{S_1^2}{S_2^2} \qquad \text{Formula (14)}$$

wherein, $S_1^2$ is variance between groups, $S_2^2$ is variance within groups, according to degree of freedom, $v_1$, $v_2$, and a given significance level of $\alpha$=0.05, a critical value of $F_{\alpha,(v_1,v_2)}$ is obtained by table look-up, and an F value calculated from Formula 14 is compared with $F_\alpha$, if $F<F_\alpha$, it is considered that there is no significant difference between within-groups and between-groups, and the N protein in the nCOV N protein reference material in the packaging unit is uniform; otherwise, the N protein in the nCOV N protein reference material in the packaging unit is not uniform, (l) long-term stability test of the nCOV N protein reference material in the packaging unit a long-term stability test is performed for a period of not less than 6 months, in which 5 time points k are selected following a rule of "first more and then less", and at each time point, the nCOV N protein reference material is sampled from at least 2 packaging units in step (e) to subject to test in triplicate by IDMS, and/or amino acid analysis, and/or immunoassay for the N protein content of the nCOV N protein reference material in each packaging unit, and then an arithmetic mean value $Y_i$ of the test results at each time point is calculated, and fitted with the corresponding measuring time $X_i$ according to the linear model below:

$$Y_i = b_0 + bX_i \quad \text{Formula (15)}$$

in Formula (15):

$b_0$—intercept, b—regression coefficient/slope; $X_i$—test time, in month; $Y_i$—arithmetic mean value of test results of the N protein content of the nCOV N protein reference material at each time point;

the regression coefficient/slope and the intercept are calculated according to Formula (16) and Formula (17):

$$b = \sum_{i=1}^{k} \frac{(X_i - \overline{X})(Y_i - \overline{Y})}{\sum_{i=1}^{k}(X_i - \overline{X})^2} \quad \text{Formula (16)}$$

$$b_0 = \overline{Y} - b \cdot \overline{X} \quad \text{Formula (17)}$$

in Formula (16) and Formula (17):

$X_i$—test time at the $i^{th}$ time point, in month;

$Y_i$—arithmetic mean value of test results of the N protein in the nCOV N protein reference material in the packaging units at the $i^{th}$ time point;

$\overline{X}$—mean value of test time at all the time points, in month;

$\overline{Y}$—arithmetic mean value of test results of the N protein in the nCOV N protein reference material in the packaging units at all the time points;

k—number of time points;

s is calculated according to Formula (18):

$$s = \sqrt{\frac{\sum_{i=1}^{k}(Y_i - b_0 - bX_i)^2}{k-2}} \quad \text{Formula (18)}$$

various symbols in Formula (18) have the same meanings as those in Formula (15), Formula (16), and Formula (17), s(b) is calculated according to Formula (19):

$$s(b) = \frac{s}{\sqrt{\sum_{i=1}^{k}(X_i - \overline{X})^2}} \quad \text{Formula (19)}$$

the value of $t_{0.95,k-2}$ is obtained by look-up in the t distribution table;

if $|b|<t_{0.95,k-2}\cdot s(b)$, the slope is not significant, indicating that the nCOV N protein reference material is stable for long term; otherwise, it indicates that the nCOV N protein reference material is not stable;

(m) short-term stability test of the N protein content of the nCOV N protein reference material in the packaging unit a short-term stability test is performed for a continuous period of not less than 7 days, in which 5 time points k are selected following a rule of "first more and then less", and at each time point, the nCOV N protein reference material is sampled from at least 2 packaging units in step (e) and placed at a temperature ranging from −20° C. to 40° C. for inspection, the N protein content of the nCOV N protein reference material in each packaging unit is tested in triplicate by IDMS, and/or amino acid analysis , and/or immunoassay, and then an arithmetic mean value $Y_i$ of the test results at each time point is calculated, and fitted with the corresponding measuring time $X_i$ according to the linear model below:

$$Y_i = b_0 + bX_i \quad \text{Formula (20)}$$

in Formula (20):

$b_0$—intercept, b—regression coefficient/slope; $X_i$—test time at the $i^{th}$ time point, in day; Yi—arithmetic mean value of test results of the N protein content of the nCOV N protein reference material at the $i^{th}$ time point;

the regression coefficient/slope and the intercept are calculated according to Formula (21) and Formula (22):

$$b = \sum_{i=1}^{k} \frac{(X_i - \overline{X})(Y_i - \overline{Y})}{\sum_{i=1}^{k}(X_i - \overline{X})^2} \quad \text{Formula (21)}$$

$$b_0 = \overline{Y} - b \cdot \overline{X} \quad \text{Formula (22)}$$

in Formula (21) and Formula (22):

$X_i$—test time at the $i^{th}$ time point, in day;

$Y_i$—arithmetic mean value of test results of the N protein content in the nCOV N protein reference material in the packaging units at the $i^{th}$ time point;

$\overline{X}$ mean value of test time at all the time points, in day;

$\overline{Y}$ arithmetic mean value of test results of the N protein content in the nCOV N protein reference material in the packaging units at all the time points;

k—number of time points;

s is calculated according to Formula (23):

$$s = \sqrt{\frac{\sum_{i=1}^{k}(Y_i - b_0 - bX_i)^2}{k-2}} \quad \text{Formula (23)}$$

various symbols in Formula (23) have the same meanings as those in Formula (20), Formula (21), and Formula (22), s(b) is calculated according to Formula (23):

$$s(b) = \frac{s}{\sqrt{\sum_{i=1}^{k}(X_i - \overline{X})^2}} \quad \text{Formula (23)}$$

the value of $t_{0.95,k-2}$ is obtained by look-up in the t distribution table, if $|b| < t_{0.95,k-2} \cdot s(b)$, the slope is not significant, indicating that the nCOV N protein reference material is stable for short term, otherwise, it indicates that the nCOV N protein reference material is not stable for short term;

(V). Determination of Standard Value of the N Protein Content in the nCOV N Protein (N Protein) Reference Material (n) determination of N protein content in the nCOV N protein reference material by amino acid analysis-based HPLC-isotopic dilution mass spectrometer first, nCOV N protein reference materials are randomly taken as samples from at least 5 packaging units in step (e), and the N protein content in each of the above packaging units is tested in triplicate according to the method of step (b) to give a total of at least 15 test results, which are tested according to the K-S single-sample normality test and for which Grabs method and/or Dixon method are used for outlier test; for samples that pass the statistical test, the arithmetic mean value of all the results is taken as the standard value of the test results of HPLC-IDMS; while for samples that fail to pass the statistical K-S single-sample normality test, Grabs method and/or Dixon method for outlier test, the number of samples is increased and the step (n) is repeated until passed;

(o) the N protein content of the nCOV N protein reference material is determined by peptide fragment analysis-based HPLC-IDMS, one or more of the following standard peptide fragments and corresponding isotope-labeled peptide fragments of the standard peptide fragments are synthesized, and the candidate reference material also comprises the following peptide fragments:

MSDNGPQNQR,

ITFGGPSDSTGSNQNGER,

PQGLPNNTASWFTALTQHGK,

GQGVPINTNSSPDDQIGYYR,

-continued

WYFYYLGTGPEAGLPYGANK,

DGIIWVATEGALNTPK,

NPANNAAIVLQLPQGTTLPK,

GFYAEGSR,

GGSQASSR,

NSTPGSSR,

MAGNGGDAALALLLLDR,

LNQLESK,

GQQQQGQTVTK,

SAAEASK,

AYNVTQAFGR,

GPEQTQGNFGDQELIR,

QGTDYK,

HWPQIAQFAPSASAFFGMSR,

IGMEVTPSGTWLTYTGAIK,

DQVILLNK,

HIDAYK,

TFPPTEPK,

ADETQALPQR,

QQTVTLLPAADLDDFSK,

QLQQSMSSADSTQA the purity of the standard peptide fragments was tested according to the method of step (f) to screen out standard peptide fragments with a purity not less than 99%, and at the same time the corresponding isotope-labeled peptide fragments of the standard peptide fragments are synthesized with $^{13}C$, $^{15}N$ or D as label; when the isotope-labeled standard peptide fragments have molecular weight of 1000 or below, the number of labeled atoms is not less than 3; and when the isotope-labeled standard peptide fragments has molecular weight of 1000 or above, the number of labeled atoms is not less than 6;

the selected standard peptide fragments are dissolved in water containing 0.1% trifluoroacetic acid to formulate a solution containing 0.1 mg/g of the standard peptide fragments; (0.001 to 1) mg/mL of $^{13}C$ or/and $^{15}N$ or/and D isotope-labeled amino acid is added to each 100 μL of the solution of standard peptide fragments so that the content of the isotope-labeled amino acids is the same as the theoretical content of amino acids in the solution of standard peptide fragments after complete hydrolysis, and the number of the isotope-labeled atoms is not less than 3; after centrifugal concentration or nitrogen blowing, (100 to 1000) μL of concentrated hydrochloric acid with a concentration of (6 to 8) mol/L is added thereto, and sealed while passing nitrogen for protection; the mixture is hydrolyzed in an oven at 110° C. to 150° C. for 24 to 72 hours, and then the content of amino acids in the hydrolysate is determined by HPLC-IDMS using a national reference material of mixed amino acid solution as standard, and the purity of the standard peptide fragments is calculated according to the sequence of the standard peptide fragments;

the nCOV N protein reference materials are taken as samples from at least 5 packaging units in step (e), from each of which 100 μL is taken to determine N protein concentration according to step (b), then an isotope-labeled peptide fragment equimolar to the N protein is added, followed by 5 μg to 100 μg of trypsin which is dissolved in 200 μL of ammonium bicarbonate with a concentration of 0.1 to 0.2 mol/L at pH 8.0 and containing 10% to 20% of acetonitrile; after the addition of trypsin, the mixture is digested at a temperature of 37° C. for 24 to 72 hours to give a digested sample; a mixture of standard peptide fragments and isotope-labeled peptide fragments with the same concentration of digested peptide fragments as that in the digested sample is formulated as a standard solution, and the concentration of the digested peptide fragments in the digested sample is tested using the following method;

the digested sample and the standard solution are analyzed by HPLC-tandem mass spectrometry using an aqueous solution containing 0.1% formic acid as mobile phase A and an acetonitrile solution containing 0.1% formic acid as mobile phase B; the injection volume is (3 to 20) μL, and a 2.1 mm×150 mm C18 reversed-phase chromatography column is used for isolation at a flow rate of 0.2 mL/min, the gradient of mobile phase changes linearly from 100% mobile phase A to 100% mobile phase B to achieve the isolation of the digested peptide fragments; a triple tandem quadrupole mass spectrometer is used for detection to harvest mass spectrometry signals from various standard peptide fragments and corresponding isotope-labeled peptide fragments, and each of the digested samples and the standard solutions are analyzed in triplicate, the concentrations of various standard peptide fragments in the digested samples are calculated according to the concentrations of the standard peptide fragments and the isotope-labeled peptide fragments in the standard solution and their mass respectively added, as well as the peak areas of the standard peptide fragments and isotope-labeled peptide fragments in the extraction chromatogram of the digested samples, the peak areas of the standard peptide fragments and isotope-labeled peptide fragments in the extraction chromatogram of the standard solution, the sample mass, and the concentration and mass of the isotope-labeled peptide fragments added in the sample, and the concentration of N protein in the sample is calculated according to the molecular weight of the standard peptide fragments and N protein according to the formulas below:

$$R_{STD} = \frac{c_{pep} M_{pep}}{c'_{pep} M'_{pep}}$$

$$c_s = \frac{R_{STD} A_s c'_s M'_s}{A_{STD} M_s}$$

$$c_N = \frac{c_s}{\mathrm{MW}_s} \times \mathrm{MW}_N$$

in the formula, $R_{STD}$ is a ratio of the mass of the standard peptide fragment to the mass of the isotope-labeled peptide fragment in the standard solution, $c_{pep}$ is a concentration of standard peptide fragment, $M_{pep}$ is a mass of the standard peptide fragment added, $c'_{pep}$ is a concentration of the isotope-labeled peptide fragment, $M'_{pep}$ is a mass of the isotope-labeled peptide fragment added, $c_s$ is a concentration of the standard peptide fragment in the digested sample, $A_s$ is a ratio of peak area of the standard peptide fragment to the isotope-labeled peptide fragment in the sample, $c'_s$ is a concentration of the isotope-labeled peptide fragment added in the sample, $M'_s$ is a mass of isotope-labeled peptide fragment added in the sample, $A_{STD}$ is a ratio of peak area of the standard peptide fragment to the isotope-labeled peptide fragment in the standard solution, $M_s$ is a sample mass, $c_N$ is a concentration of N protein in the sample, $MW_s$ is a molecular weight of the standard peptide fragment, and $MW_N$ is a molecular weight of the N protein;

the obtained measurement results are tested according to the K-S single-sample normality test and the Grabs method and/or Dixon method are used for outlier test; for samples that pass the statistical test, the arithmetic mean value of all the results is taken as the standard value of test results of peptide fragment analysis-based HPLC-IDMS; while for samples that fail to pass the statistical K-S single-sample normality test, Grabs method and/or Dixon method for outlier test, the number of samples is increased and the step (o) is repeated until passed;

(VI). Determination and Statistical Test of Standard Value of nCOV N Protein Reference Material the at least 15 data of N protein content obtained by the amino acid analysis-based HPLC-IDMS in step (n) and the at least 15 data of N protein content obtained by the peptide fragment analysis-based HPLC-IDMS in step (o) are subject to independent-samples t-test; if the |t| value calculated from Formula (24) is less than $t_{\alpha,(n_1+n_2-2)}$, wherein $t_{\alpha,(n_1+n_2-2)}$ is obtained by look-up in GB/T 4086.3-1983, the Tables for statistical distributions—t-distribution, then it is considered that the t-test result is passed, indicating that there is no systematic bias between the certified results of the two methods; the arithmetic mean value of the two methods is taken as a certified value x, and when the t-test result fails, the step (V) is repeated;

$$t = \frac{\overline{X_1} - \overline{X_2}}{\sqrt{\frac{s_1^2}{n_1} + \frac{s_2^2}{n_2}}} \quad \text{Formula (24)}$$

in Formula (24):

$\overline{X}_1$—mean number of the first sample, that is, a standard value of the test results by the amino acid analysis-based HPLC-IDMS;

$\overline{X}_2$—mean number of the second sample, that is, a standard value of the test results by the peptide fragment analysis-based HPLC-IDMS;

$s_1^2$—variance of the first sample, $$s_1^2 = \frac{\sum_{i=1}^{n_1} (X_i - \overline{X_1})^2}{n_1 - 1};$$

$s_2^2$—variance of the second sample, $$s_2^2 = \frac{\sum_{j=1}^{n_2}(X_j - \overline{X_2})^2}{n_2 - 1};$$

$n_1$—volume of the first sample, that is, a number determined by the amino acid analysis-based HPLC-IDMS;

$n_2$—volume of the second sample, that is, a number determined by the peptide fragment analysis-based HPLC-IDMS;

(VII). Assessment of Uncertainty of the Certified Results of the Standard Value of the nCOV N Protein Reference Material the uncertainty U of the certified results of the nCOV N protein reference material is derived from an uncertainty $u_{char}$ introduced during the certification, an uncertainty $u_{bb}$ introduced by the uniformity of reference material, an uncertainty $u_{sts}$ introduced by short-term stability and an uncertainty $u_{lts}$ introduced by long-term stability, which are combined according to Formula (25)

$$U = k'\sqrt{u_{char}^2 + u_{bb}^2 + u_{lts}^2 + u_{sts}^2} \quad \text{Formula (25)}$$

in the formula, k' is a coverage factor, typically k'=2;

where, $u_{char}$ includes an uncertainty $u_{char,HPLC\text{-}AAA\text{-}IDMS}$ from the amino acid analysis-based HPLC-IDMS and an uncertainty $u_{char,HPLC\text{-}PEP\text{-}IDMS}$ from the peptide fragment analysis-based HPLC-IDMS; and $u_{char,HPLC\text{-}AAA\text{-}IDMS}$ includes an uncertainty component $u_{char,HPLC\text{-}AAA\text{-}IDMS,A}$ (Formula (26)) introduced by the repeatability of the test results of the amino acid analysis-based HPLC-IDMS, as well as an uncertainty component $u_{char,HPLC\text{-}AAA\text{-}IDMS,wi}$ (Formula (27)) introduced by multiple balance weighing, and an uncertainty component $u_{char,HPLC\text{-}AAA\text{-}IDMS,P}$ (Formula (28)) introduced by the amino acid reference material, which are combined according to Formula (29), $$u_{char,HPLC-AAA-IDMS,A} = \frac{s}{\sqrt{n}} \quad \text{Formula (26)}$$

in Formula (26), s is a standard deviation, i.e., $$s = \sqrt{\frac{\sum_{i=1}^{n}(x_i - \overline{x})^2}{n-1}},$$

$x_i - \overline{x}$ is a deviation between a certain data and the sample mean, and n is number of measurements;

$$u_{char,HPLC-AAA-IDMS,wi} = \frac{|MPE|}{\sqrt{3}} \quad \text{Formula (27)}$$

in Formula (27), MPE is a maximum permissible error of balance verification certificate $$u_{char,HPLC-AAA-IDMS,P} = \frac{U}{k'} \quad \text{Formula (28)}$$

in Formula (28), U is an uncertainty in the certificate of the national amino acid reference material, k' is a coverage factor, typically, k'=2;

Formula (29)

$$u_{char,HPLC-AAA-IDMS} = \sqrt{u_{char,HPLC-AAA-IDMS,A}^2 + \sum_{i=1}^{q}(c_i u_{char,HPLC-AAA-IDMS,wi})^2 + c_p^2 u_{char,HPLC-AAA-IDMS,p}^2}$$

In Formula (29), q is a number of balance weighing, $c_i$ is a sensitivity coefficient at the $i^{th}$ weighing, and $c_p$ is a sensitivity coefficient of the purity of the reference material which is calculated according to JJF1059.1-2012, the Evaluation and Expression of Uncertainty in Measurement;

$u_{char,HPLC\text{-}PEP\text{-}IDMS}$ includes an uncertainty component $u_{char,HPLC\text{-}PEP\text{-}IDMS,A}$ (Formula (30)) introduced from the repeatability of the test results of the amino acid analysis-based HPLC-IDMS, as well as an uncertainty component $u_{char,HPLC\text{-}PEP\text{-}IDMS,wi}$ (Formula (31)) introduced by multiple balance weighing, and an uncertainty component $u_{char,HPLC\text{-}PEP\text{-}IDMS,P}$ (Formula (32)) introduced by the peptide fragment reference material, which are combined according to Formula (33), $$u_{char,HPLC-pep-IDMS,A} = \frac{s}{\sqrt{n}} \quad \text{Formula (30)}$$

In Formula (30), s is a standard deviation, i.e., $$s = \sqrt{\frac{\sum_{i=1}^{n}(x_i - \overline{x})^2}{n-1}},$$

$x_i - \overline{x}$ is a deviation between a certain data and the sample mean, and n is number of measurements;

$$u_{char,HPLC-pep-IDMS,wi} = \frac{|MPE|}{\sqrt{3}} \quad \text{Formula (31)}$$

in Formula (31), MPE is the maximum permissible error of balance verification certificate $$u_{char,HPLC-pep-IDMS,P} = \frac{U}{k'} \quad \text{Formula (32)}$$

-continued

Formula (33)

$$u_{char,HPLC-PEP-IDMS} = \sqrt{u^2_{char,HPLC-PEP-IDMS,A} + \sum_{i=1}^{q}(c_i u_{char,HPLC-PEP-IDMS,wi})^2 + c_p^2 u^2_{char,HPLC-PEP-IDMS,p}}$$

in Formula (33), q is a number of balance weighing, $c_i$ is a sensitivity coefficient at the $i^{th}$ weighing, and $c_p$ is a sensitivity coefficient of the purity of the reference material;

$u_{char}$ is calculated according to Formula (34):

Formula (34)

$$u_{char} = \frac{1}{2}\sqrt{u^2_{char,HPLGAAA-IDMS} + u^2_{char,HPLC-PEP-IDMS}}$$

when mean square between groups is greater than or equal to mean square within group, the uncertainty introduced by uniformity is calculated according to Formula (35);

Formula (35)

$$u_{bb} = S_{bb} = \sqrt{\frac{1}{n}\left(\frac{Q_1}{v_1} - \frac{Q_2}{v_2}\right)} = \sqrt{\frac{s_1^2 - s_2^2}{n}}$$

when the mean square between groups is less than the mean square within group, the uncertainty introduced by uniformity is calculated according to Formula (36);

Formula (36)

$$u_{bb} = S_{bb} = \sqrt{\frac{s_2^2}{n}}\sqrt[4]{\frac{2}{v_2}}$$

the uncertainty introduced by short-term stability and the uncertainty introduced by long-term stability of the reference material are calculated according to Formula (37) and Formula (38):

Formula (37)

$$u_{sts} = s_{k,sts} \cdot t_{sts}$$

Formula (38)

$$u_{lts} = s_{k,lts} \cdot t_{lts}$$

in the formulas, the $s_{k,sts}$ is s(b) in the short-term stability test obtained from Formula (19), and $t_{ts}$ is the duration in the short-term stability test, in day;

the $s_{k,lts}$ is s(b) in the long-term stability test obtained from Formula (23), and $t_{lts}$ is the duration in the long-term stability test, in month;

the above results are combined according to Formula (25) to give an expanded uncertainty U of the certified value of the reference material, so that the certified result of the nCOV N protein reference material can be represented as:

$$x \pm U$$

in the formula, x is the certified value, and U is the expanded uncertainty of the certified value;

finally, the certified results of the uniformity, stability, and N protein content of the prepared nCOV N protein reference material are obtained.

The method for preparing and certifying an nCOV N protein of the present invention, wherein: in step (a), the biochemical reagent is purified by an isoelectric focusing electrophoresis instrument in which (0.01 to 1) mol/L of phosphoric acid and (0.01 to 1) mol/L of sodium hydroxide are used as electrophoresis solution at two ends of the isoelectric focusing electrophoresis instrument, respectively, after completion of the isoelectric focusing, fractions with isoelectric point around 10.5 are collected, and the biochemical reagent is then purified by a molecular sieve column, the appearance time of peak is monitored at an absorbance of 280 nm to collect the fractions during the period of the appearance time, the collected fractions are repeatedly purified over the molecular sieve column; after repeating the purification over the molecular sieve column three times, the fraction obtained at the last appearance time of peak is collected to complete the purification of the nCOV N protein.

The method for preparing and certifying an nCOV N protein of the present invention, wherein: in step (a), the biochemical reagent is purified by a molecular sieve column, the appearance time of peak is monitored at an absorbance of 280 nm to collect the fractions during the period of the appearance time, the collected fractions are repeatedly purified over the molecular sieve column; after repeating the purification over the molecular sieve column three times, the fraction obtained at the last appearance time of peak is collected to complete the purification of the nCOV N protein.

The method for preparing and certifying an nCOV N protein of the present invention, wherein: in step (b), the number of the isotope-labeled atoms is not less than 3.

The method for preparing and certifying an nCOV N protein of the present invention, wherein, in step (f), the universal protein purity analysis method includes: reversed HPLC, and/or ion exchange chromatography HPLC, and/or gel exclusion HPLC, and/or hydrophobic interaction HPLC, and/or immunoaffinity HPLC, which, co-operating with UV, and/or fluorescence, and/or differential refraction, and/or evaporative light scattering, and/or fluorescence electrospray ionization, and/or circular dichroism spectrometer, is used to characterize the purity of the reference material.

The method for preparing and certifying an nCOV N protein of the present invention, wherein: in step (f), the universal protein purity analysis method further includes SDS-PAGE gel electrophoresis, and/or capillary electrophoresis, and/or chip electrophoresis, and/or two-dimensional electrophoresis, which, co-operating with UV and/or fluorescence, is used to characterize the purity of the reference material.

The method for preparing and certifying an nCOV N protein of the present invention, wherein: in step (f), the universal protein purity analysis method further includes high performance liquid chromatography-mass spectrometry (HPLC-MS), and/or matrix-assisted laser-induced desorption time-of-flight mass spectrometry, which is used to characterize the purity of the reference material.

The method for preparing and certifying an nCOV N protein of the present invention, wherein: in step (f), the universal protein purity analysis method further includes electrochemical method or nuclear magnetic resonance spectroscopy, which is used to characterize the purity of the reference material.

The method for preparing and certifying an nCOV N protein of the present invention, wherein: in step (o), in the test with the MS triple tandem quadrupole mass spectrometer, a positive ion mode and a selective ion monitoring (SIM) or multiple reaction monitoring (MRM) scanning mode are used.

DETAILED DESCRIPTION

The present invention is further illustrated by reference to the following examples:

A method for preparing and certifying a novel coronavirus nucleocapsid protein (nCOV N protein) reference material of the present invention includes the following steps:

(I). Purification and Dilution of a Raw Material of the nCOV N Protein (a) Purification of the raw material of the nCOV N protein The nCOV N protein is an N protein sequence of SEQ ID NO: 1 as set forth below, or a protein sequence with (3 to 10) histidine or lysine attached to one or both ends of the N protein sequence of SEQ ID NO: 1:

```
  1 MSENGPQNQR NAPRITFGGP SDSTGSNQNG ERSGARSKQR RPQGLPNNTA SWFTALTQHG KEDLKFPRGQ GVPINTNSSP
 81 DDQIGYYRRA TRRIRGGDGK MKDLSPRWYF YYLGTGPEAG LPYGANKDGI IWVATEGALN TPKDHIGTRN PANNAAIVLQ
161 LPQGTTLPKG FYAEGSRGGS QASSRSSSRS RNSSRNSTPG SSRGTSPARM AGNGGDAALA LLLLDRLNQL ESKMSGKGQQ
241 QQGQTVTKKS AAEASKKPRQ KRTATKAYNV TQAFGRRGPE QTQGNFGQCE LIRQGTDYKH WPQIAQFAPS ASAFFGMSRI
321 GMEVTPSGTW LQYTGAIRLD DKDPNFKDQV ILLNKHIDAY KTFPPTEPKK DKKKKADETQ ALPQRQKKQQ TVTLLPAADL
401 DDFSKQLQQS MSSADSTQA.
```

The raw material of the nCOV N protein was purchased from a biotechnology service company, which had a purity of about 95% as measured by high performance liquid chromatography-gel exclusion liquid chromatography. To give a candidate nCOV N protein reference material with a high purity, the above biochemical reagent was purified by a molecular sieve method or an isoelectric focusing method to give a candidate nCOV N protein reference material with a purity of 98.5% or above; and to give an active nCOV N protein with a high purity, the following conditions were employed for purification:

First, using the GE AKTA explorer Protein Purification Workstation, the commercially available raw material of the N protein as purchased was passed through Sephadex G75 gel column and eluted with PBS, the outflow signal was monitored at UV280 nm, and the fraction of the primary peak was collected. Taking bovine serum albumin as the certification standard, the concentration in the collection solution was measured by Coomassie brilliant blue (CBB) method. A total of 5 mL collection solution was collected, in which the N protein concentration was about 2 mg/mL. Then, the collection solution was diluted to 10 mL with water so that the N protein concentration therein was about 1 mg/mL. Then, 1 mL of solution was taken each time, and loaded into a self-made isoelectric focusing purification device, with 0.1 mol/L of phosphoric acid and 0.1 mol/L of NaOH as electrode solutions at the two ends of the electrode. The isoelectric focusing was performed at a voltage of 3000 V and a temperature of 10° C. At the same time, the isoelectric focusing profile of protein in lanes was detected by real-time CCD imaging signal. After completion of the isoelectric focusing, the fractions with isoelectric point of 10.5±0.2 were collected. The collected nCOV N protein fractions were further purified over Sephadex G75 molecular sieve column with PBS as mobile phase. The appearance time of peak was monitored at an absorbance of 280 nm to collect the fractions during the period of the appearance time. The purification was repeated over the molecular sieve column three times, and the fraction at the last appearance time of peak was collected to give the candidate nCOV N protein reference material. Taking bovine serum albumin as the standard, the N protein in the collected fraction was certified using the CBB method to give the candidate nCOV N protein reference material with a purity of 98.5% or above, which was diluted in water to about 0.1 mg/mL.

(b) Preliminary measurement of concentration of the candidate nCOV N protein reference material To 50 μL of the purified candidate nCOV N protein reference material was added 0.01 mg/mL of $^{13}$C-labeled valine and phenylalanine (with the number of isotope-labeled atoms of 5 and 8, respectively), and then the mixture was subject to centrifugal concentration or nitrogen blowing. Then, (500) μL of concentrated hydrochloric acid with a concentration of 6 mol/L was added thereto, and sealed while passing nitrogen for protection. The mixture was hydrolyzed in an oven at 110° C. for 36 hours to give a hydrolysate. After hydrolysis, taking the national reference material of valine and phenylalanine as the standard, the content of amino acids in the hydrolysate was measured using HPLC-IDMS, and the initial concentration of the candidate nCOV N protein reference material was calculated as 0.142 mg/g according to the N protein sequence of SEQ ID NO: 1.

(c) Dilution of the candidate nCOV N protein reference material

The candidate nCOV N protein reference material, of which the concentration has been preliminarily measured, was diluted with PBS to a concentration of (0.1) mg/g to give a diluted solution of the candidate nCOV N protein reference material;

(II). Preliminary Uniformity Test and Packaging of the Solution of the Candidate nCOV N Protein Reference Material (d) Preliminary uniformity test of the solution of the candidate nCOV N protein reference material 3 sub-samples are taken from each of upper, middle, and lower parts of the diluted solution of the candidate nCOV N protein reference material in step (c), respectively, to obtain a total of 9 test samples, the 9 test samples are numbered and arranged in order, and the content of the nCOV N protein in each test sample is subject to a first test by IDMS, or amino acid analysis, or immunoassay, then the order is disrupted, and the content of the nCOV N protein in each test sample is subject to a second test, the above operations are repeated until each test sample is tested three times, obtaining 27 test results, and the uniformity of the content $\bar{\bar{x}}$ of the nCOV N protein in the taken test sample was calculated and counted according to the formulas below;

when m=9 samples were taken, 9 sets of precisely measured data were obtained according to the above test method under a condition of repeatability n=3, as shown below:

No. 1: $x_{11}, x_{12} \ldots x_{1n}$, with a mean value of $\bar{x}_1$

No. 2: $x_{21}, x_{22} \ldots x_{2n}$, with a mean value of $\bar{x}_2$

. . .

No. m: $x_{m1}, x_{m2} \ldots x_{mn}$, with a mean value as below:

$$\text{mean value} = x = \frac{\sum_{i=1}^{m} \overline{x_i}}{m} \quad \text{Formula (1)}$$

$$\text{statistical value } N \ N = m \cdot n \quad \text{Formula (2)}$$

sum of squares of between-group differences:

$$Q_1 = \sum_{i=1}^{m} n\left(\bar{x}_i - \bar{\bar{x}}\right)^2 \quad \text{Formula (3)}$$

sum of squares of intra-group differences:

$$Q_2 = \sum_{i=1}^{m}\sum_{j=1}^{n}(x_{ij} - \bar{x}_i)^2 \quad \text{Formula (4)}$$

degree of freedom between groups: $v_1=m-1$; degree of freedom within groups:

$$v_2 = N - m$$

$$S_1^2 = \frac{Q_1}{v_1} \quad \text{Formula (5)}$$

$$S_2^2 = \frac{Q_2}{v_2} \quad \text{Formula (6)}$$

statistical value F:

$$F = \frac{S_1^2}{S_2^2} \quad \text{Formula (7)}$$

where, $S_1^2$ is variance between groups, $S_2^2$ is variance within groups, according to degree of freedom, $v_1$, $v_2$, and a given significance level of $\alpha=0.05$, a critical value of $F_{\alpha,(v_1,v_2)}$ is obtained by table look-up, and an F value calculated from Formula 7 is compared with $F_\alpha$, if $F<F_\alpha$, it is considered that there is no significant difference between within-groups and between-groups, and the nCOV N protein in the taken test sample is uniform; otherwise, the content of the nCOV N protein in the taken test sample is not uniform, and if the content of the nCOV N protein in the taken test sample is not uniform, the steps (a) to (c) are repeated until the solution of the candidate nCOV N protein reference material in the taken test sample passes the preliminary uniformity test;

TABLE 1

Results of preliminary uniformity test of the nCoV N protein reference material (mg/g)

| | 1 | 2 | 3 | Mean |
|---|---|---|---|---|
| Sample 1 | 0.101 | 0.103 | 0.105 | 0.103 |
| Sample 2 | 0.101 | 0.104 | 0.100 | 0.103 |
| Sample 3 | 0.105 | 0.102 | 0.103 | 0.104 |
| Q1 | 4.66667E−06 | Q2 | 2.13333E−05 | |
| F | 0.66 | $F_{crit}$ | 5.14 | |

It can be seen from the results of uniformity test that the calculated F value is less than the critical value of $F_{\alpha,(v_1,v_2)}$, and thus the results of the preliminary uniformity test of the nCOV nucleocapsid protein reference material is uniform and the product can be packaged.

(e) Packaging of the solution of the candidate nCOV N protein reference material The solution of the candidate nCOV N protein reference material which passes the preliminary uniformity test in step (d) was packaged into 500 μL silanized cryotubes with 10 μL of the candidate solution in each silanized cryotube. The packaged solution of the candidate nCOV N protein reference material was labeled and consecutively numbered according to the packaging order to obtain a total of P packaging units, which were then stored in a refrigerator at −80° C.

III. Characterization of Physicochemical Properties of the nCOV N Protein Reference Material (f) Purity test of the nCOV N protein reference material in the packaging unit The purity of the nCOV N protein reference material was analyzed using SDS-PAGE gel electrophoresis and HPLC gel exclusion chromatography.

The experimental steps of the SDS-PAGE gel electrophoresis are as follows: 20 μL of N protein was taken from a packaged unit of the reference material and mixed with an equivalent volume of 1× electrophoresis loading buffer, boiled in a boiling water bath for 5 min. 10 μL of N protein was loaded for each lane. The sample was isolated using Mini-PROTEAN precast gel from Bio-Rad Laboratories, Inc. at an electrophoresis voltage of 120 V and for an electrophoresis period of 45 min. After the completion of electrophoresis, it was stained with Coomassie brilliant blue, and then decolored with a methanol-acetic acid solution and imaged. A purity analysis was performed with the gel imaging system from BIO-RAD. No other visible protein bands appeared in the N protein lane, and the purity was >99%.

The experimental steps of HPLC-gel exclusion chromatography are as follows:

Sample: A solution of the raw material of the N protein reference material, 0.1 mg/ml Loading volume: 10 μL Chromatographic column: TSKGel 2000 SWxl gel exclusion chromatographic column, 7.8 mm×300 mm Mobile phase:water:acetonitrile:trifluoroacetic acid (70:30:0.1, v:v:v)

Detection wavelength: 215 nm

Flow rate: 0.5 mL/min

According to the collected chromatogram, the N protein purity was analyzed as 99.2% by an area normalization method, and there are no individual impurities with a content exceeding 0.1%. '(g) Characterization of molecular weight of the nCOV N protein reference material in the packaging unit Using the SDS-PAGE gel electrophoresis and the matrix-assisted laser-induced desorption time-of-flight mass spectrometry, the molecular weight of the nCOV N protein reference material was measured.

The experimental conditions for SDS-PAGE gel electrophoresis are as follows: 20 μL of N protein was taken from the packaged reference material unit and mixed with an equivalent volume of 1× electrophoresis loading buffer, and boiled in a boiled water bath for 5 min. 10 μL of N protein was loaded for each lane, and a molecular weight Marker of the loaded protein was used in one of the lanes. The sample was isolated using Mini-PROTEAN precast gel from Bio-Rad Laboratories, Inc. at an electrophoresis voltage of 120 V and for an electrophoresis period of 45 min. After the completion of electrophoresis, it was stained with Coomassie brilliant blue, and then decolored with a methanol-acetic acid solution and imaged. According to the molecular weight of the Marker, the molecular weight of the N protein was calculated. From the electrophoretogram, the molecular weight of the N protein was measured as 45 kD which was consistent with the mean molecular weight of 45625 Da as calculated according to the theoretical sequence thereof.

The experimental conditions for the matrix-assisted laser-induced desorption time-of-flight mass spectrometry are as follows: First, 10 μL of N protein raw material with a concentration of 0.1 mg/mL was fully mixed with Sinapinic acid (SA) matrix solution at 1:1 (v/v), and 2 μL of the mixed liquor was taken to spot. After crystallization of sample, a matrix-assisted laser desorption-tandem time-of-flight mass spectrometer (linear mode) was used to characterize the molecular weight of the N protein, for which the acceleration voltage was 20 kV, and the scanning range of the mass-to-charge ratio (m/z) was 15000-100000. The initial data obtained from the experiments were analyzed via the flex Analysis software (with a signal to noise ratio of 3:1). From the mass spectrogram, the molecular weight of the N protein was measured as 45 kD which was consistent with the theoretical molecular weight of 45625 Da.

(h) Protein identification of the nCOV N protein reference material in the packaging unit The experimental conditions for the protein identification of the nCOV N protein reference material are as follows: About 2 μg protein was dissolved in 50 μL of 50 mM ammonium bicarbonate containing 0.1% (w/v) RapiGest SF. 4 μL of dithiothreitol (DTT) with a concentration of 0.1 mol/L was added into the sample. The sample was heated at 50° C. for 30 min, and 8 μL of 0.1 mol/L iodoacetamide was added. After the sample was cooled to room temperature, it was left in dark for 40 min. 16 μg trypsin (with a concentration of 20 μg/100 μL) was added into the sample, and the sample was incubated at 37° C. overnight. The digested sample was diluted 10 times with pure water for MALDI-TOF mass spectrometry analysis. The target protein was obtained in SWISSPROT database by MASCOT search, and the result was nCOV nucleocapsid protein.

(i). De novo sequencing of the nCOV N protein reference material in the packaging unit About 200 μg protein was dissolved in 500 μL of 50 mM ammonium bicarbonate containing 0.1% (w/v) RapiGest SF. 160 μg trypsin (with a concentration of 20 μg/100 μL) was added into the sample, and the sample was incubated at 37° C. overnight. The digested sample was isolated by reverse phase HPLC. All the peptide fragments with good isolation degree and correspondingly high peak signals were collected one by one, lyophilized, reconstituted in water containing 0.1% formic acid, and then spotted on a PVDF membrane. Each collected peptide fragment was subject to de novo sequencing with a protein sequencer based on the Edman principle. The sequences of all the peptide fragments were spliced to obtain a full-length sequence of the nCOV N protein. The sequences were spliced, and the result was consistent with the protein corresponding to the sequence of SEQ ID NO: 1.

(j) Identification and certification of impurity proteins in the nCOV N protein reference material in the packaging unit When an individual impurity had a content exceeding 1% in the purity test of the nCOV N protein reference material, it was required to identify and certify the impurity; and when no individual impurity had a content exceeding 1% in the purity test, it was not required to identify and certify the impurity. In this example, the content of the impurity protein was less than 1%, and thus the identification and certification of the impurity were not required.

(IV). Uniformity and Stability Test of the nCOV N Protein Reference Material in the Packaging Unit (k) Uniformity test of the nCOV N protein reference material in the packaging unit The consecutively numbered packaging units are randomly sampled with a randbetween function in Excel, when P≤200, the number m of the sampled packaging units is not less than 11; when 200<P≤500, the number m of the sampled packaging units is not less than 15; when 500<P≤1000, the number m of the sampled packaging units is not less than 25; when the packaging units P>1000, the number m of the sampled packaging units is not less than 30; according to the sampling order, the m sampled packaging units are renumbered and arranged in order, the N protein content of the nCOV N protein reference material in the sampled packaging units is subject to a uniformity test by IDMS, or amino acid analysis, or immunoassay; during the test, the N protein in the nCOV N protein reference material in each sampled packaging unit is subject to a first test according to the above order, and then the order is disrupted, and the N protein content in the nCOV N protein reference material in each sampled packaging unit is subject to a second test, the above operations are repeated until the N protein in the nCOV N protein reference material in each sampled packaging unit is subject to a $n^{th}$ test, wherein n is an integer greater than or equal to 3, to give n test results, and an uniformity of the N protein in the nCOV N protein reference material in the packaging units are calculated and counted out according to the formulas below;

when m samples are taken, m sets of precisely measured data are obtained according to the above test method under a condition of repeatability n, as shown below:

No. 1: $x_{11}$, $x_{12}$ . . . $x_{1n}$, with a mean value of $\bar{x}_1$

No. 2: $x_{21}$, $x_{22}$ . . . $x_{2n}$, with a mean value of $\bar{x}_2$

. . .

No. m: $x_{m1}$, $x_{m2}$ . . . $x_{mn}$, with a mean value of $\bar{x}_m$:

$$\text{mean value} = x = \frac{\sum_{i=1}^{m} \overline{x_i}}{m} \quad \text{Formula (8)}$$

$$\text{statistical value } N \; N = m \cdot n \quad \text{Formula (9)}$$

Sum of squares of between-group differences:

$$Q_1 = \sum_{i=1}^{m} n\left(\bar{x}_i - \bar{\bar{x}}\right)^2 \quad \text{Formula (10)}$$

Sum of squares of intra-group differences:

$$Q_2 = \sum_{i=1}^{m}\sum_{j=1}^{n}(x_{ij} - \bar{x}_i)^2 \quad \text{Formula (11)}$$

Degree of freedom between groups: $v_1$=m−1; degree of freedom within groups:

$$v_2 = N - m$$

$$S_1^2 = \frac{Q_1}{v_1} \quad \text{Formula (12)}$$

$$S_2^2 = \frac{Q_2}{v_2} \quad \text{Formula (13)}$$

Statistical value F:

$$F = \frac{S_1^2}{S_2^2} \quad \text{Formula (14)}$$

where, $S_1^2$ is variance between groups, $S_2^2$ is variance within groups, according to degree of freedom, $v_1$, $v_2$, and a given significance level of α=0.05, a critical value of $F_{\alpha,(v_1,v_2)}$ is obtained by table look-up, and an F value calculated from Formula 14 is compared with $F_\alpha$, if $F<F_\alpha$, it is considered that there is no significant difference between within-groups and between-groups, and the nCOV N protein in the packaging unit is uniform; otherwise, the content of the nCOV N protein in the packaging unit is not uniform.

In this example, a total of 300 units of nCOV N protein reference materials were prepared. The 15 randomly selected N protein samples were analyzed by isotope dilution mass spectrometry in step (b). Each sample was analyzed in triplicate, and the results were shown in the table below:

TABLE 2

Uniformity test of the nCoV N protein reference material

| | 1 | 2 | 3 | Mean |
|---|---|---|---|---|
| Sample 1 | 0.099 | 0.096 | 0.096 | 0.097 |
| Sample 2 | 0.099 | 0.107 | 0.097 | 0.101 |
| Sample 3 | 0.100 | 0.108 | 0.104 | 0.104 |
| Sample 4 | 0.105 | 0.109 | 0.096 | 0.103 |
| Sample 5 | 0.106 | 0.099 | 0.108 | 0.104 |
| Sample 6 | 0.095 | 0.106 | 0.107 | 0.103 |
| Sample 7 | 0.109 | 0.102 | 0.107 | 0.106 |
| Sample 8 | 0.099 | 0.105 | 0.098 | 0.101 |
| Sample 9 | 0.101 | 0.105 | 0.103 | 0.103 |
| Sample 10 | 0.101 | 0.101 | 0.105 | 0.102 |
| Sample 11 | 0.106 | 0.104 | 0.102 | 0.104 |
| Sample 12 | 0.101 | 0.098 | 0.103 | 0.101 |
| Sample 13 | 0.109 | 0.100 | 0.096 | 0.102 |
| Sample 14 | 0.107 | 0.102 | 0.109 | 0.106 |
| Sample 15 | 0.099 | 0.108 | 0.098 | 0.102 |
| Q1 | 0.000221778 | Q2 | 0.000585333 | |
| F | 0.81 | $F_{crit}$ | 2.04 | |

It can be seen from the results of the uniformity test that the calculated F value from the uniformity test of N protein content in the nCOV N protein reference material is less than the critical value of $F_{\alpha,(v_1,v_2)}$, indicating that the reference material is uniform.

(l) Long-term stability test of the nCOV N protein reference material in the packaging unit a long-term stability test is performed for a period of not less than 6 months, in which 5 time points k are selected following a rule of "first more and then less", and at each time point, the nCOV N protein reference material is sampled from at least 2 packaging units in step (e) to subject to a test in triplicate by IDMS, and/or amino acid analysis, and/or immunoassay for the N protein content of the nCOV N protein reference material in each packaging unit, and then an arithmetic mean value $Y_i$ of the test results at each time point is calculated, and fitted with the corresponding measuring time $X_i$ according to the linear model below:

$$Y_i = b_0 + bX_i \quad \text{Formula (15)}$$

in Formula (15):

$b_0$—intercept, b—regression coefficient/slope; $X_i$—test time, in month; $Y_i$—arithmetic mean value of test results of the N protein content of the nCOV N protein reference material at each time point;

the regression coefficient/slope and the intercept are calculated according to Formula (16) and Formula (17):

$$b = \sum_{i=1}^{k} \frac{\left(X_i - \bar{X}\right)\left(Y_i - \bar{Y}\right)}{\sum_{i=1}^{k}\left(X_i - \bar{X}\right)^2} \quad \text{Formula (16)}$$

$$b_0 = \bar{Y} - b \cdot \bar{X} \quad \text{Formula (17)}$$

in Formula (16) and Formula (17):

$X_i$—test time at the $i^{th}$ time point, in month;

$Y_i$—arithmetic mean value of test results of the N protein in the nCOV N protein reference material in the packaging unit at the $i^{th}$ time point;

$\bar{X}$—mean value of test time at all the time points, in month;

$\overline{Y}$—arithmetic mean value of test results of the N protein in the nCOV N protein reference material in the packaging unit at all time points;

k—number of time points;

s is calculated according to Formula (18):

$$s = \sqrt{\frac{\sum_{i=1}^{k}(Y_i - b_0 - bX_i)^2}{k-2}} \quad \text{Formula (18)}$$

various symbols in Formula (18) have the same meanings as those in Formula (15), Formula (16), and Formula (17), s(b) is calculated according to Formula (19):

$$s(b) = \frac{s}{\sqrt{\sum_{i=1}^{k}(X_i - \overline{X})^2}} \quad \text{Formula (19)}$$

the value of $t_{0.95,k-2}$ is obtained by look-up in the t distribution table,

If $|b|<t_{0.95,k-2}\cdot s(b)$, the slope was not significant, indicating that the nCOV N protein reference material was stable for long term; otherwise, it indicated that the nCOV N protein reference material was not stable.

The nCOV N protein reference material was subject to a long-term stability test for a period of 6 months, and the results of the stability test are shown in Table 3.

TABLE 3

Results of long-term stability test of the nCoV N protein reference material

| Time/month | 1 | 2 | 3 | Mean |
|---|---|---|---|---|
| 0 | 0.104 | 0.108 | 0.099 | 0.1037 |
| 1 | 0.095 | 0.103 | 0.100 | 0.0993 |
| 2 | 0.102 | 0.108 | 0.108 | 0.1060 |
| 4 | 0.098 | 0.101 | 0.104 | 0.1010 |
| 6 | 0.107 | 0.097 | 0.095 | 0.0997 |

Taking the time as x axis and the content as y axis, it is calculated that k=−0.000505172, and intercept b=0.103253448.

standard deviation $$s^2 = \frac{\sum_{i=1}^{n}(Y_i - b_0 - kx_i)^2}{n-2} = 8.84379E{-06}$$

then s=0.002973852, uncertainty of slope $$s(k) = \frac{s}{\sqrt{\sum_{i=1}^{n}(x_i - \overline{x})^2}} = 0.000617412$$

for degree of freedom of 4 and p=0.95, the t-distribution factor is 2.78; Since $$|k| < t_{0.95,n-2} \cdot s(k)$$

the slope was not significant, and thus uncertainty was not observed. According to the stability test results, the certified value of the nCOV N protein reference material remains stable at −80° C. for at least 6 months.

(m) Short-term stability test of the N protein content of the nCOV N protein reference material in the paukaging Unit A short-term stability test is performed for a continuous period of not less than 7 days, in which 5 time points k are selected following a rule of "first more and then less", and at each time point, the nCOV N protein reference material is sampled from at least 2 packaging units in step (e) and placed at a temperature ranging from −20° C. to 40° C. for inspection, the N protein content of the nCOV N protein reference material in each packaging unit is tested in triplicate by IDMS, and/or amino acid analysis, and/or immunoassay, and then an arithmetic mean value $Y_i$ of the test results at each time point is calculated, and fitted with the corresponding measuring time $X_i$ according to the linear model below:

$$Y_i = b_0 + bX_i \quad \text{Formula (20)}$$

in Formula (20):

$b_0$—intercept, b—regression coefficient/slope; $X_i$—test time at the $i^{th}$ time point, in day; Yi—arithmetic mean value of test results of the N protein content of the nCOV N protein reference material at the $i^{th}$ time point;

the regression coefficient/slope and the intercept are calculated according to Formula (21) and Formula (22):

$$b = \sum_{i=1}^{k}\frac{(X_i - \overline{X})(Y_i - \overline{Y})}{\sum_{i=1}^{k}(X_i - \overline{X})^2} \quad \text{Formula (21)}$$

$$b_0 = \overline{Y} - b\cdot\overline{X} \quad \text{Formula (22)}$$

in Formula (21) and Formula (22):

$X_i$—test time at the $i^{th}$ time point, in day;

$Y_i$—arithmetic mean value of test results of the N protein content in the nCOV N protein reference material in the packaging unit at the $i^{th}$ time point;

$\overline{X}$—mean value of test time at all the time points, in day;

$\overline{Y}$—arithmetic mean value of test results of the N protein content of the nCOV N protein reference material in the packaging unit at all time points;

k—number of time points;

s is calculated according to Formula (23):

$$s = \sqrt{\frac{\sum_{i=1}^{k}(Y_i - b_0 - bX_i)^2}{k-2}} \quad \text{Formula (23)}$$

various symbols in Formula (23) have the same meanings as those in Formula (20), Formula (21), and Formula (22), s(b) is calculated according to Formula (23):

$$s(b) = \frac{s}{\sqrt{\sum_{i=1}^{k}(X_i - \bar{X})^2}} \quad \text{Formula (23)}$$

the value of $t_{0.95,k-2}$ is obtained by look-up in the t distribution table, if $|b| < t_{0.95,k-2} \cdot s(b)$, the slope is not significant, indicating that the nCOV N protein reference material is stable for short term; otherwise, it indicates that the nCOV N protein reference material is not stable for short term. The test results of the short-term stability test of the nCOV N protein at 4° C. are as follows:

TABLE 4

Results of the short-term stability test of the nCoV N protein reference material at 4° C., mg/g

| Time/month | 1 | 2 | 3 | Mean |
|---|---|---|---|---|
| 0 | 0.096 | 0.097 | 0.109 | 0.1007 |
| 1 | 0.096 | 0.103 | 0.099 | 0.0993 |
| 3 | 0.100 | 0.102 | 0.107 | 0.1030 |
| 5 | 0.108 | 0.101 | 0.101 | 0.1033 |
| 7 | 0.101 | 0.109 | 0.107 | 0.1057 |

Taking the time as x axis and the content as y axis, it is calculated that k=0.000801829, and intercept b=0.099834146.

standard deviation $$s^2 = \frac{\sum_{i=1}^{n}(Y_i - b_0 - kx_i)^2}{n-2} = 1.1573E{-06}$$

then s=0.001075777, uncertainty of slope:

$$s(k) = \frac{s}{\sqrt{\sum_{i=1}^{n}(x_i - \bar{x})^2}} = 0.000187839$$

for degree of freedom of 4 and p=0.95, t-distribution factor is 2.78;

Since $$|k| < t_{0.95,n-2} \cdot s(k)$$

the slope is not significant, and thus uncertainty is not observed. According to the stability test results, the certified value of the nCOV N protein reference material remains stable at 4° C. for at least 7 days.

(V). Determination of Standard Value of the N Protein Content of the nCOV N Protein Reference Material (n) Determination of the N protein content in the nCOV N protein reference material by amino acid analysis-based HPLC-isotopic dilution mass spectrometer First, the nCOV N protein reference materials were randomly taken as samples from at least 5 packaging units in step (e), and the N protein content in each of the above packaging units was tested in triplicate according to the method of step (b) to give a total of at least 15 test results, as shown in the table below:

TABLE 5

Test results of the N protein content by amino acid analysis-based HPLC-IDMS, mg/g

| | 1 | 2 | 3 | Mean |
|---|---|---|---|---|
| Sample 1 | 0.099 | 0.096 | 0.096 | 0.097 |
| Sample 2 | 0.099 | 0.107 | 0.097 | 0.101 |
| Sample 3 | 0.100 | 0.108 | 0.104 | 0.104 |
| Sample 4 | 0.105 | 0.109 | 0.096 | 0.103 |
| Sample 5 | 0.106 | 0.099 | 0.108 | 0.104 |
| Grand Mean | | 0.1018 | | |

According to the K-S single-sample normality test, the Grabs method and/or Dixon method were used for outlier test, all the samples passed the above statistical test. Thus, the arithmetic mean value of all the results, 0.1018 mg/g, was taken as the standard value of the test results of the HPLC-IDMS.

(o) Determination of the N protein content of the nCOV N protein reference material by peptide fragment analysis-based HPLC-IDMS The standard peptide fragment ITFGGPSDSTGSNQNGER and the corresponding isotope-labeled peptide fragment ITF*GGPSDSTGSNQNGER were synthesized, where F* was $^{13}C_8$-labeled phenylalanine. The synthesized standard peptide fragment was subject to a purity examination by reverse phase HPLC, and the result was 99.2%. The synthesized standard peptide fragments were dissolved in water containing 0.1% trifluoroacetic acid to formulate a solution with a concentration of 0.1 mg/g. To 100 mL of the standard peptide fragment solution was added $^{13}C$ isotope-labeled phenylalanine and proline with a concentration of 0.01 mg/mL, and the mixture was subject to centrifugal concentration or nitrogen blowing. To the mixture was added 500 μL of concentrated hydrochloric acid with a concentration of 6 mol/L, and sealed while passing nitrogen for protection. The mixture was hydrolyzed in an oven at 110° C. for 60 hours. After hydrolysis, taking the national reference material of mixed amino acid solution as standard, the amino acid content in the hydrolysate was measured by IDMS, and the purity of the standard peptide fragments was calculated as 0.843 g/g according to the sequence of the standard peptide fragment.

5 nCOV N protein reference materials were randomly taken. 100 μL was taken from each sample, calculated as 0.1 mg/g, and an equivalent mole of isotope-labeled peptide fragment was added. 100 μg trypsin (dissolved in 200 μL of ammonium bicarbonate with a concentration of 0.1 mol/L, pH=8.0, containing 10% acetonitrile) was added and digested at 37° C. for 36 hours to give a digested sample. According to the concentration of the digested peptide fragment in the sample, a mixture of the standard peptide fragment and the isotope-labeled peptide segment with similar concentration was formulated as standard solution.

After digestion, both the digested sample and the standard solution were analyzed by HPLC-tandem mass spectrometry, using an aqueous solution containing 0.1% formic acid as mobile phase A, and an acetonitrile solution containing 0.1% formic acid as mobile phase B. The injection volume was (3~20) μL, and a 2.1 mm×150 mm C18 reversed-phase chromatography column was used for isolation at a flow rate of 0.2 mL/min. Within 120 min, the gradient of mobile phase linearly changed from 100% mobile phase A to 100% mobile phase B, to achieve the isolation of the digested peptide fragments. A triple tandem quadrupole mass spectrometer is used for detection to harvest mass spectrometry signals from the standard peptide fragment ITFGGPSDSTGSNQNGER and the corresponding isotope-labeled peptide fragments, respectively, by using a positive ion mode and a multiple reaction monitoring (MRM) scanning mode. Each sample was analyzed in triplicate. The concentrations of various standard peptide fragments in the digested samples were calculated according to the concentrations of the standard peptide fragments and the isotope-labeled peptide fragments in the standard solution and their mass respectively added, as well as the peak areas of the standard peptide fragments and isotope-labeled peptide fragments in the extraction chromatogram of the digested samples, the peak areas of the standard peptide fragments and isotope-labeled peptide fragments in the extraction chromatogram of the standard solution, the sample mass, and the concentration and mass of the isotope-labeled peptide fragment added in the sample, and the concentration of N protein in the sample was calculated according to the molecular weight of the standard peptide fragments and N protein according to the formulas below:

$$R_{STD} = \frac{c_{pep} M_{pep}}{c'_{pep} M'_{pep}}$$

$$c_s = \frac{R_{STD} A_s c'_s M'_s}{A_{STD} M_s}$$

$$c_N = \frac{c_s}{MW_s} \times MW_N$$

In the formula, $R_{STD}$ is a ratio of the mass of the standard peptide fragment to the mass of the isotope-labeled peptide fragment in the standard solution, $c_{pep}$ is a concentration of the standard peptide fragment, $M_{pep}$ is a mass of the standard peptide fragment added, $c'_{pep}$ is a concentration of the isotope-labeled peptide fragment, $M'_{pep}$ is a mass of the isotope-labeled peptide fragment added, $c_s$ is a concentration of the standard peptide fragment in the digested sample, $A_s$ is a ratio of peak area of the standard peptide fragment to the isotope-labeled peptide fragment in the sample, $c'_s$ is a concentration of the isotope-labeled peptide fragment added in the sample, $M'_s$ is a mass of the isotope-labeled peptide fragment added in the sample, $A_{STD}$ is a ratio of peak area of the standard peptide fragment to the isotope-labeled peptide fragment in the standard solution, $M_s$ is a sample mass, $c_N$ is a concentration of N protein in the sample, $MW_s$ is a molecular weight of the standard peptide fragment, and $MW_N$ is a molecular weight of the N protein.

The results are shown in Table 6.

TABLE 6

Test results of the N protein content by peptide fragment analysis-based HPLC-IDMS, mg/g

| | 1 | 2 | 3 | Mean |
|---|---|---|---|---|
| Sample 1 | 0.097 | 0.100 | 0.105 | 0.1007 |
| Sample 2 | 0.092 | 0.098 | 0.099 | 0.0963 |
| Sample 3 | 0.101 | 0.089 | 0.105 | 0.0983 |
| Sample 4 | 0.109 | 0.090 | 0.110 | 0.1030 |
| Sample 5 | 0.116 | 0.112 | 0.111 | 0.1130 |
| Grand Mean | | | 0.1027 | |

The obtained test results were subject to the K-S single-sample normality test, the Grabs method and/or Dixon method were used for outlier test, and all the samples passed the above statistical test. Thus, the arithmetic mean value of all the results, 0.1027 mg/g, was taken as the standard value of the test results of the peptide fragment analysis-based HPLC-IDMS method.

(VI). Determination and Statistical Test of Standard Value of nCOV N Protein Reference Material The at least 15 data of N protein content obtained by the amino acid analysis-based HPLC-IDMS in step (n) and the at least 15 data of N protein content obtained by the peptide fragment analysis-based HPLC-IDMS in step (o) were subject to independent-samples t-test; if the |t| value calculated from Formula (24) is less than $t_{\alpha,(n_1+n_2-2)}$, wherein $t_{\alpha,(n_1+n_2-2)}$ is obtained by look-up in GB/T 4086.3-1983, the Tables for statistical distributions—t-distribution, then it is considered that the t-test result is passed, indicating that there is no systematic bias between the certified results of the two methods; the arithmetic mean value of the two methods was taken as a certified value x, and when the t-test result fails, the step (V) is repeated;

$$t = \frac{\overline{X_1} - \overline{X_2}}{\sqrt{\frac{s_1^2}{n_1} + \frac{s_2^2}{n_2}}} \quad \text{Formula (24)}$$

In Formula (24):

$\overline{X_1}$—mean number of the first sample, that is, a standard value of the test results by the amino acid analysis-based HPLC-IDMS;

$\overline{X_2}$—mean number of the second sample, that is, a standard value of the test results by the peptide fragment analysis-based HPLC-IDMS;

$s_1^2$—variance of the first sample, $$s_1^2 = \frac{\sum_{i=1}^{n_1} (X_i - \overline{X_1})^2}{n_1 - 1};$$

$s_2^2$—variance of the second sample, $$s_2^2 = \frac{\sum_{j=1}^{n_2} (X_j - \overline{X_2})^2}{n_2 - 1};$$

$n_1$—volume of the first sample, that is, a number determined by the amino acid analysis-based HPLC-IDMS;

$n_2$—volume of the second sample, that is, a number determined by the peptide fragment analysis-based HPLC-IDMS;

The data in Tables 5 and 6 were tested for consistency of the mean value, and the calculated $|t|=0.0106$ is less than $t_{\alpha,(n_1+n_2-2)}=2.30$. Therefore, there is no systematic error between the certified results from the two methods, and the mean value of the certified results of the two methods, 0.102 mg/g, was taken as the certified result.

(VII). Assessment of Uncertainty of the Certified Results of the Standard Value of the nCOV N Protein Reference Material The uncertainty U of the certified results of the nCOV N protein reference material is derived from an uncertainty $u_{char}$ introduced during the certification, an uncertainty $u_{bb}$ introduced by the uniformity of reference material, an uncertainty $u_{sts}$ introduced by short-term stability and an uncertainty $u_{lts}$ introduced by long-term stability, which are combined according to Formula (25)

$$U = k'\sqrt{u_{char}{}^2 + u_{bb}{}^2 + u_{lts}{}^2 + u_{sts}{}^2} \quad \text{Formula (25)}$$

In the formula, k' is a coverage factor, typically k'=2;

Where, $u_{char}$ includes an uncertainty $u_{char,HPLC\text{-}AAA\text{-}IDMS}$ from the amino acid analysis-based HPLC-IDMS and an uncertainty $u_{char,HPLC\text{-}PEP\text{-}IDMS}$ from the peptide fragment analysis-based HPLC-IDMS; and $u_{char,HPLC\text{-}AAA\text{-}IDMS}$ includes an uncertainty component $u_{char,HPLC\text{-}AAA\text{-}IDMS,A}$ (Formula 26) introduced by the repeatability of the test results of the HPLC-IDMS, as well as an uncertainty component $u_{char,HPLC\text{-}AAA\text{-}IDMS,wi}$ (Formula 27) introduced by multiple balance weighing, and an uncertainty component $u_{char,HPLC\text{-}AAA\text{-}IDMS,P}$ (Formula 28) introduced by the amino acid reference material, which are combined according to Formula (29).

$$u_{char,HPLC-AAA-IDMS,A} = \frac{s}{\sqrt{n}} \quad \text{Formula (26)}$$

In Formula (26), s is a standard deviation, i.e., $$s = \sqrt{\frac{\sum_{i=1}^{n}(x_i - \bar{x})^2}{n-1}},$$

$x_i-\bar{x}$ is a deviation between a certain data and the sample mean, and n is number of measurements.

$$u_{char,HPLC-AAA-IDMS,wi} = \frac{|MPE|}{\sqrt{3}} \quad \text{Formula (27)}$$

In Formula (27), MPE is a maximum permissible error of balance verification certificate.

$$u_{char,HPLC-AAA-IDMS,P} = \frac{U}{k'} \quad \text{Formula (28)}$$

In Formula (28), U is an uncertainty in the certificate of national amino acid reference material, k' is a coverage factor, typically k'=2.

$$u_{char,HPLC-AAA-IDMS} = \sqrt{u^2_{char,HPLC-AAA-IDMS,A} + \sum_{i=1}^{q}(c_i u_{char,HPLC-AAA-IDMS,wi})^2 + c_p^2 u^2_{char,HPLC-AAA-IDMS,p}} = 0.00134 \text{ mg/g} \quad \text{Formula (29)}$$

In Formula (29), q is a number of balance weighing, $c_i$ is a sensitivity coefficient at the $i^{th}$ weighing, and $c_p$ is a sensitivity coefficient of the purity of the reference material which is calculated according to JJF1059.1-2012, the Evaluation and Expression of Uncertainty in Measurement.

$u_{char,HPLC\text{-}PEP\text{-}IDMS}$ of the test results of the peptide fragment analysis-based HPLC-IDMS method is calculated according to Formula (33):

$$u_{char,HPLC-PEP-IDMS} = \sqrt{u^2_{char,HPLC-PEP-IDMS,A} + \sum_{i=1}^{q}(c_i u_{char,HPLC-PEP-IDMS,wi})^2 + c_p^2 u^2_{char,HPLC-PEP-IDMS,p}} = 0.00235 \text{ mg/g} \quad \text{Formula (33)}$$

In Formula (33), q is a number of balance weighing, $c_i$ is a sensitivity coefficient at the $i^{th}$ weighing, $c_p$ is a sensitivity coefficient of the purity of the reference material, and the calculation formulas for $u_{char,HPLC\text{-}PEP\text{-}IDMS,A}$, $u_{char,HPLC\text{-}PEP\text{-}IDMS,wi}$ and $u_{char,HPLC\text{-}PEP\text{-}IDMS,P}$ are the same as those in the HPLC-IDMS.

$u_{char}$ is calculated according to Formula (34):

$$u_{char} = \frac{1}{2}\sqrt{u^2_{char,HPLC-AAA-IDMS} + u^2_{char,HPLC-PEP-IDMS}} = 0.00136 \text{ mg/g} \quad \text{Formula (34)}$$

when the mean square between groups is less than the mean square within group, the uncertainty introduced by uniformity is calculated according to the following formula;

$$u_{bb} = S_{bb} = \sqrt{\frac{s_2^2}{n}}\sqrt[4]{\frac{2}{v_2}} = 0.00317 \text{ mg/g} \quad \text{Formula (36)}$$

The uncertainty introduced by short-term stability and the uncertainty introduced by long-term stability of the reference material are calculated according to the following formulas:

$$u_{sts} = s_{k,sts} \cdot t_{sts} = 0.00370 \text{ mg/g} \quad \text{Formula (37)}$$

$$u_{lts} = s_{k,lts} \cdot t_{lts} = 0.00131 \text{ mg/g} \quad \text{Formula (38)}$$

the $s_{k,sts}$ is s(b) in the short-term stability test obtained from Formula (19), and $t_{ts}$ is the duration in the short-term stability test, in day;

the $s_{k,lts}$ is s(b) in the long-term stability test obtained from Formula (23), and $t_{lts}$ is the duration in the long-term stability test, in month;

the above results are combined according to Formula (25) to give an expanded uncertainty U of the certified value of the reference material, so that the certified result of the nCOV N protein reference material can be represented as:

$$x \pm U.$$

In the formula, x is the certified value, U is an expanded uncertainty of the certified value; it is obtained that the expanded uncertainty of the certified value of the reference material U=0.011 mg/g, and thus the certified result of the nCOV N protein reference material can be represented as (0.102±0.011) mg/g; finally, the certified results of the uniformity, stability, and N protein content of the prepared nCOV N protein reference material are obtained.

The foregoing is an explanation of the present invention, rather than a limitation to the present invention. The scope of the present invention is defined by the claims, and the present invention can be modified in any form without departing from the spirit of the present invention.

The invention claimed is:

1. A method for preparing and certifying a novel coronavirus nucleocapsid protein (nCOV N protein), comprising the following steps:

I. purification and dilution of a raw material of the nCOV N protein (a) purification of the raw material of the nCOV N protein the nCOV N protein is an N protein sequence of SEQ ID NO: 1 as set forth below, or a protein sequence with 3 to 10 histidine or lysine attached to one or both ends of the N protein sequence of SEQ ID NO: 1:

```
  1 MSQNGPQNQR NAPRITFGGP SDSTGSNQNG ERSGARSKQR
    RPQGLPNNTA SWFTALTQHG KEDLKFPRGQ GVPINTNSSP

 81 DDQIGYYRRA TRRIRGGDGK MKDLSPRWYF YYLGTGPEAG
    LPYGANKDGI IWVATEGALN TPKDHIGTRN PANNARIVLQ

161 LPQGTTLPKG FYAEGSRGGS QASSRSSSRS RNSSRNSTPG
    SSRGTSPARM AGNGGDAALA LLLLDRLNQL ESKMSGKGQQ

241 QQGQTVTKKS AAEASKKPRQ KRTATKAYNV TQAFGRRGPE
    QTQGNFGQCE LIRQGTDYKH WPQIAQFAPS ASAFFGMSRI

321 GMEVTPSGTW LTYIGAIKLD DKDPNFKDQV ILLNKHIDAY
    KTFPPTEPKK QRKKKADETQ ALPCRQKKQQ TVFLLPAADL

481 DQFSKQLQCS MSSADSTQA
```

the raw material is from a commercially available nCOV N protein biochemical reagent with a purity of 90% to 95%, for obtaining a candidate nCOV N protein reference material with a high purity, the biochemical reagent is purified by an isoelectric focusing method and/or a molecular sieve method to give the candidate nCOV N protein reference material with a purity of 98.5% or above;

(b) preliminary measurement of concentration of the candidate nCOV N protein reference material $^{13}C$ isotope-labeled valine and phenylalanine with a concentration of 0.001 to 1 mg/mL are added into to 1 to 100 μL of the candidate nCOV N protein reference material, the mixture is subject to centrifugal concentration or nitrogen blowing, and then 100 to 1000 μL of concentrated hydrochloric acid with a concentration of 6 to 8 mol/L is added thereto, and sealed while passing nitrogen for protection, the mixture is hydrolyzed in an oven at 110° C. to 150° C. for 24 h to 72 h to give a hydrolysate, and after hydrolysis, an amino acid content in the hydrolysate is measured by high performance liquid chromatography-isotopic dilution mass spectrometry (HPLC-IDMS) using national reference materials of valine and phenylalanine as standard, and an initial concentration of the candidate nCOV N protein reference material is calculated according to the N protein sequence of SEQ ID NO: 1;

(c) dilution of the candidate nCOV N protein reference material the candidate nCOV N protein reference material, of which the concentration has been preliminarily measured, is diluted with PBS as solvent to a concentration ranging from 0.05 to 0.2 mg/g to give a diluted solution of the candidate nCOV N protein reference material;

(II). preliminary uniformity test and packaging of the solution of the candidate nCOV N protein reference material (d) preliminary uniformity test of the solution of the candidate nCOV N protein reference material 3 sub-samples are taken from each of upper, middle, and lower parts of the diluted solution of the candidate nCOV N protein reference material in step (c), respectively, to obtain a total of 9 test samples, the 9 test samples are numbered and arranged in order, and the content of the nCOV N protein in each test sample is subject to a first test by isotopic dilution mass spectrometry (IDMS), amino acid analysis (AAA), or immunoassay, then the order is disrupted, and the content of the nCOV N protein in each test sample is subject to a second test, the above operations are repeated until each test sample is tested three times, obtaining 27 test results, and the uniformity of the content $\bar{x}$ of the nCOV N protein in the taken test sample is calculated according to the formulas below;

when m=9 samples are taken, 9 sets of precisely measured data are obtained according to the above test method under a condition of repeatability n=3, as shown below:

No. 1: $x_{11}, x_{12} \ldots x_{1n}$, with a mean value of $\bar{x}_1$

No. 2: $x_{21}, x_{22} \ldots x_{2n}$, with a mean value of $\bar{x}_2$

...

No. m: $x_{m1}, x_{m2} \ldots x_{mn}$, with a mean value as below:

$$\text{mean value}\quad \bar{\bar{x}} = \frac{\sum_{i=1}^{m} \bar{x}_i}{m} \qquad \text{Formula 1}$$

$$\text{Statistical value}\quad N\ N = m \cdot n \qquad \text{Formula 2}$$

sum of squares of between-group differences:

$$Q_1 = \sum_{i=1}^{m} n\left(\bar{x}_i - \bar{\bar{x}}\right)^2 \qquad \text{Formula 3}$$

sum of squares of intra-group differences:

$$Q_2 = \sum_{i=1}^{m} \sum_{j=1}^{n} n(x_{ij} - \bar{x}_i)^2 \qquad \text{Formula 4}$$

degree of freedom between groups: $v_1 = m-1$; degree of freedom within groups:

$$v_2 = N - m$$

$$S_1^2 = \frac{Q_1}{v_1} \qquad \text{Formula 5}$$

$$S_2^2 = \frac{Q_2}{v_2} \qquad \text{Formula 6}$$

statistical value F:

$$F = \frac{S_1^2}{S_2^2} \qquad \text{Formula 7}$$

wherein, $S_1^2$ is variance between groups, $S_2^2$ is variance within groups, according to degree of freedom $v_1$, $v_2$, and a given significance level of α=0.05, a critical value of $F_{\alpha,(v_1,v_2)}$ is obtained by table look-up, and an F value calculated from Formula 7 is compared with $F_\alpha$, if $F<F_\alpha$, it is considered that there is no significant difference between within-groups and between-groups, and the nCOV N protein in the taken test sample is uniform; otherwise, the content of the nCOV N protein in the taken test sample is not uniform, and if the content of the nCOV N protein in the taken test sample is not uniform, the steps (a) to (c) are repeated until the solution of the candidate nCOV N protein reference material in the taken test sample passes the preliminary uniformity test;

(e) packaging of the solution of the candidate nCOV N protein reference material the solution of the candidate nCOV N protein reference material passing the preliminary uniformity test of step (d) is packaged into silanized cryotubes with volume of 500 μL to 2 mL with 10 μL to 500 μL of the candidate solution in each silanized cryotube, the packaged solution of the candidate nCOV N protein reference material is labeled and consecutively numbered according to the packaging order to obtain a total of P packaging units, which are then stored in a refrigerator at −80° C.;

(III). characterization of physicochemical properties of the solution of the candidate nCOV N protein reference material in the packaging unit (f) purity test of the nCOV N protein reference material in the packaging unit the purity of the nCOV N protein reference material in the packaging unit is characterized by a universal protein purity analysis method;

(g) characterization of molecular weight of the nCOV N protein reference material in the packaging unit a molecular weight of the nCOV N protein reference material in the packaging unit is determined by gel electrophoresis, and/or gel exclusion HPLC, and/or mass spectrometry, and mean value of the determination results should be consistent with theoretical molecular weight of the N protein sequence of SEQ ID NO: 1;

(h) protein identification of the nCOV N protein reference material in the packaging unit the nCOV N protein is digested with trypsin and/or V8 protease, the peptide fragments generated from the protease digestion are identified by peptide mass fingerprinting or tandem mass spectrometry, and then a target protein is obtained by searching the SWISSPROT database through SQEUEST or MASCOT, and the result should be consistent with the protein corresponding to the N protein sequence of SEQ ID NO:1;

(i) de novo sequencing of the nCOV N protein reference material in the packaging unit the nCOV N protein is digested with trypsin and/or V8 protease, and the digested peptide fragments are subject to de novo sequencing by HPLC-tandem mass spectrometry, and amino acid sequence of the peptide fragment is determined by b, y ion series generated from each peptide fragment; amino acid sequences of all the obtained peptide fragments are spliced manually or by a random matching software or a third-party software to give a full-length sequence of the nCOV N protein which should be consistent with the protein sequence corresponding to the N protein of SEQ ID NO: 1;

or the nCOV N protein is digested with trypsin and/or V8 protease, the digested peptide fragments are isolated by reverse phase HPLC, all the peptide fragments with good isolation degree and correspondingly high peak signals are collected one by one, lyophilized, reconstituted in water containing 0.1% formic acid, and then spotted on a PVDF membrane, each collected peptide fragment is subject to de novo sequencing with a protein sequencer based on the Edman principle, sequences of all the peptide fragments are spliced to obtain a full-length sequence of the nCOV N protein, and the result should be consistent with the protein sequence corresponding to the N protein sequence of SEQ ID NO: 1;

(j) identification and certification of impurity proteins in the nCOV N protein reference material in the packaging unit in the purity test of the nCOV N protein reference material in step (f), if an individual impurity has a content exceeding 1%, a fraction containing the impurity is collected out and identified according to steps (f) to (h) for impurity protein; after identification, the impurity is purchased or expressed by recombination to made a standard of the impurity, and then a standard curve is plotted, with horizontal axis representing a concentration of the standard and vertical axis representing a corresponding signal; otherwise, it is not required to identify and certify the impurity;

(IV). uniformity and stability test of the nCOV N protein reference material in the packaging unit (k) uniformity test of the nCOV N protein reference material in the packaging unit the consecutively numbered packaging units are randomly sampled with a randbetween function in Excel, when $P \leq 200$, the number m of the sampled packaging units is not less than 11; when $200<P \leq 500$, the number m of the sampled packaging units is not less than 15; when $500<P \leq 1000$, the number m of the sampled packaging units is not less than 25; when the packaging units $P>1000$, the number m of the sampled packaging units is not less than 30; according to the sampling order, the m sampled packaging units are re-numbered and arranged in order, the N protein content of the nCOV N protein reference material in the sampled packaging unit is subject to a uniformity test by IDMS, or amino acid analysis, or immunoassay; during the test, the N protein in the nCOV N protein reference material in each sampled packaging unit is subject to a first test according to the above arrangement order, and then the order is disrupted, and the N protein content in the nCOV N protein reference material in each sampled packaging unit is subject to a second test, the above operations are repeated until the N protein in the nCOV N protein reference material in each sampled packaging unit is subject to a $n^{th}$ test, wherein n is an integer greater than or equal to 3, to give n test results, and an uniformity of the N protein in the nCOV N protein reference material in the packaging units are calculated and counted out according to the formulas below;

when m samples are taken, m sets of precisely measured data are obtained according to the test method under a condition of repeatability n, as shown below:

$$No.\ 1: x_{11}, x_{12} \ldots x_{1n}, \text{ with a mean value of } \bar{x}_1$$

$$No.\ 2: x_{21}, x_{22} \ldots x_{2n}, \text{ with a mean value of } \bar{x}_2$$

$$No.\ m: x_{m1}, x_{m2} \ldots \bar{x}_{mn}, \text{ with a mean value } \bar{x}_m$$

$$\text{mean value } \bar{\bar{x}} = \frac{\sum_{i=1}^{m} \bar{x}_i}{m} \quad \text{Formula 8}$$

$$\text{Statistical value } N \; N = m \cdot n \quad \text{Formula 9}$$

sum of squares of between-group differences:

$$Q_1 = \sum_{i=1}^{m} n\left(\bar{x}_i - \bar{\bar{x}}\right)^2 \quad \text{Formula 10}$$

sum of squares of intra-group differences:

$$Q_2 = \sum_{i=1}^{m} \sum_{j=1}^{n} (x_{ij} - \bar{x}_i)^2 \quad \text{Formula 11}$$

degree of freedom between groups: $v_1=m-1$; degree of freedom within groups:

$$v_2 = N - m$$

$$S_1^2 = \frac{Q_1}{v_1} \quad \text{Formula 12}$$

$$S_2^2 = \frac{Q_2}{v_2} \quad \text{Formula 13}$$

statistical value F:

$$F = \frac{S_1^2}{S_2^2} \quad \text{Formula 14}$$

wherein, $S_1^2$ is variance between groups, $S_2^2$ is variance within groups, according to degree of freedom, $v_1$, $v_2$, and a given significance level of $\alpha=0.05$, a critical value of $F_{\alpha,(v_1,v_2)}$ is obtained by table look-up, and an F value calculated from Formula 14 is compared with $F_\alpha$, if $F<F_\alpha$, it is considered that there is no significant difference between within-groups and between-groups, and the N protein in the nCOV N protein reference material in the packaging unit is uniform; otherwise, the N protein in the nCOV N protein reference material in the packaging unit is not uniform, (l) long-term stability test of the nCOV N protein reference material in the packaging unit a long-term stability test is performed for a period of not less than 6 months, in which 5 time points k are selected following a rule of "first more and then less", and at each time point, the nCOV N protein reference material is sampled from at least 2 packaging units in step (e) to subject to test in triplicate by IDMS, and/or amino acid analysis, and/or immunoassay for the N protein content of the nCOV N protein reference material in each packaging unit, and then an arithmetic mean value $Y_i$ of the test results at each time point is calculated, and fitted with the corresponding measuring time $X_i$ according to the linear model below:

$$Y_i = b_0 + bX_i \quad \text{Formula 15}$$

in Formula 15:

$b_0$—intercept, b—regression coefficient/slope; $X_i$—test time, in month; $Y_i$—arithmetic mean value of test results of the N protein content of the nCOV N protein reference material at each time point;

the regression coefficient/slope and the intercept are calculated according to Formula 16 and Formula 17:

$$b = \sum_{i=1}^{k} \frac{(X_i - \bar{X})(Y_i - \bar{Y})}{\sum_{i=1}^{k}(X_i - \bar{X})^2} \quad \text{Formula 16}$$

$$b_0 = \bar{Y} - b \cdot \bar{X} \quad \text{Formula 17}$$

in Formula 16 and Formula 17:

$X_i$—test time at the $i^{th}$ time point, in month;

$Y_i$—arithmetic mean value of test results of the N protein in the nCOV N protein reference material in the packaging units at the $i^{th}$ time point;

$\bar{X}$—mean value of test time at all the time points, in month;

$\bar{Y}$—arithmetic mean value of test results of the N protein in the nCOV N protein reference material in the packaging units at all the time points;

k—number of time points;

s is calculated according to Formula 18:

$$s = \sqrt{\frac{\sum_{i=1}^{k}(Y_i - b_0 - bX_i)^2}{k-2}} \quad \text{Formula 18}$$

various symbols in Formula 18 have the same meanings as those in Formula 15, Formula 16, and Formula 17, s(b) is calculated according to Formula 19:

$$s(b) = \frac{s}{\sqrt{\sum_{i=1}^{k}(X_i - \bar{X})^2}} \quad \text{Formula 19}$$

the value of $t_{0.95,k-2}$ is obtained by look-up in the t distribution table;

if $|b|<t_{0.95,k-2} \cdot s(b)$, the slope is not significant, indicating that the nCOV N protein reference material is stable for long term; otherwise, it indicates that the nCOV N protein reference material is not stable;

(m) short-term stability test of the N protein content of the nCOV N protein reference material in the packaging unit a short-term stability test is performed for a continuous period of not less than 7 days, in which 5 time points k are selected following a rule of "first more and then less", and at each time point, the nCOV N protein reference material is sampled from at least 2 packaging units in step (e) and placed at a temperature ranging from −20° C. to 40° C. for inspection, the N protein content of the nCOV N protein reference material in each packaging unit is tested in triplicate by IDMS, and/or amino acid analysis, and/or immunoassay, and then an arithmetic mean value $Y_i$ of the test results at each time point is calculated, and fitted with the corresponding measuring time Xi according to the linear model below:

$$Y_i = b_0 + bX_i \quad \text{Formula 20}$$

in Formula 20:

$b_0$—intercept, b—regression coefficient/slope; $X_i$—test time at the $i^{th}$ time point, in day; Yi—arithmetic mean value of test results of the N protein content of the nCOV N protein reference material at the $i^{th}$ time point;

the regression coefficient/slope and the intercept are calculated according to Formula 21 and Formula 22:

$$b = \sum_{i=1}^{k} \frac{(X_i - \bar{X})(Y_i - \bar{Y})}{\sum_{i=1}^{k} (X_i - \bar{X})^2} \quad \text{Formula 21}$$

$$b_0 = \bar{Y} - b \cdot \bar{X} \quad \text{Formula 22}$$

in Formula 21 and Formula 22:

$X_i$—test time at the $i^{th}$ time point, in day;

$Y_i$—arithmetic mean value of test results of the N protein content in the nCOV N protein reference material in the packaging units at the $i^{th}$ time point;

$\bar{X}$—mean value of test time at all the time points, in day;

$\bar{Y}$—arithmetic mean value of test results of the N protein content in the nCOV N protein reference material in the packaging units at all the time points;

k—number of time points;

s is calculated according to Formula 23:

$$s = \sqrt{\frac{\sum_{i=1}^{k} (Y_i - b_0 - bX_i)^2}{k-2}} \quad \text{Formula 23}$$

various symbols in Formula 23 have the same meanings as those in Formula 20, Formula 21, and Formula 22, s(b) is calculated according to Formula 23:

$$s(b) = \frac{s}{\sqrt{\sum_{i=1}^{k} (X_i - \bar{X})^2}} \quad \text{Formula 23}$$

the value of $t_{0.95,k-2}$ is obtained by look-up in the t distribution table, if $|b| < t_{0.95,k-2} \cdot s(b)$, the slope is not significant, indicating that the nCOV N protein reference material is stable for short term; otherwise, it indicates that the nCOV N protein reference material is not stable for short term;

(V). determination of standard value of the N protein content in the nCOV N protein reference material (n) determination of N protein content in the nCOV N protein reference material by amino acid analysis-based HPLC-isotopic dilution mass spectrometer first, nCOV N protein reference materials are randomly taken as samples from at least 5 packaging units in step (e), and the N protein content in each of the above packaging units is tested in triplicate according to the method of step (b) to give a total of at least 15 test results, which are tested according to the K-S single-sample normality test and for which Grabs method and/or Dixon method are used for outlier test; for samples that pass the statistical test, the arithmetic mean value of all the results is taken as the standard value of the test results of HPLC-IDMS; while for samples that fail to pass the statistical K-S single-sample normality test, Grabs method and/or Dixon method for outlier test, the number of samples is increased and the step (n) is repeated until passed;

(o) the N protein content of the nCOV N protein reference material is determined by peptide fragment analysis-based HPLC-IDMS, one or more of the following standard peptide fragments and corresponding isotope-labeled peptide fragments of the standard peptide fragments are synthesized, and the candidate reference material also comprises the following peptide fragments:

MSDNGPQNQR,

ITFGGPSDSTGSNQNGER,

PQGLPNNTASWFTALTQHGK,

GQGVPINTNSSPDDQIGYYR,

WYFYYLGTGPEAGLPYGANK,

DGIIWVATEGALNTPK,

NPANNAAIVLQLPQGTTLPK,

GFYAEGSR,

GGSQASSR,

NSTPGSSR,

MAGNGGDAALALLLLDR,

LNQLESK,

GQQQQGQTVTK,

SAAEASK,

AYNVTQAFGR,

GPEQTQGNFGDQELIR,

QGTDYK,

HWPQIAQFAPSASAFFGMSR,

IGMEVTPSGTWLTYTGAIK,

DQVILLNK,

HIDAYK,

TFPPTEPK,

ADETQALPQR,

QQTVTLLPAADLDDESK,

QLQQSMSSADSTQA the purity of the standard peptide fragments was tested according to the method of step (f) to screen out standard peptide fragments with a purity not less than 99%, and at the same time the corresponding isotope-labeled peptide fragments of the standard peptide fragments are synthesized with $^{13}C$, $^{15}N$ or D as label; when the isotope-labeled standard peptide fragment has a molecular weight of 1000 or below, the number of labeled atoms is not less than 3; and when the isotope-labeled standard peptide fragment has a molecular weight of 1000 or above, the number of labeled atoms is not less than 6;

the standard peptide fragments are dissolved in water containing 0.1% trifluoroacetic acid to formulate a solution containing 0.1 mg/g of the standard peptide fragments; 0.001 to 1 mg/mL of $^{13}C$ or/and $^{15}N$ or/and D isotope-labeled amino acid is added to each 100 μL of the solution of standard peptide fragments so that the content of the isotope-labeled amino acids is the same as the theoretical content of amino acids in the solution of standard peptide fragments after complete hydrolysis, and the number of the isotope-labeled atoms is not less than 3; after centrifugal concentration or nitrogen blowing, 100 to 1000 μL of concentrated hydrochloric acid with a concentration of 6 to 8 mol/L is added thereto, and sealed while passing nitrogen for protection; the mixture is hydrolyzed in an oven at 110° C. to 150° C. for 24 to 72 hours, and then the content of amino acids in the hydrolysate is determined by HPLC-IDMS using a national reference material of mixed amino acid solution as standard, and the purity of the standard peptide fragments is calculated according to the sequence of the standard peptide fragments;

nCoV N protein reference materials are taken as samples from at least 5 packaging units in step (c), from each of which 100 μL is taken to determine N protein concentration according to step (b), then an isotope-labeled peptide fragment equimolar to the N protein is added, followed by 5 μg to 100 μg of trypsin which is dissolved in 200 μL of ammonium bicarbonate with a concentration of 0.1 to 0.2 mol/L at pH 8.0 and containing 10% to 20% of acetonitrile; after the addition of trypsin, the mixture is digested at a temperature of 37° C. for 24 to 72 hours to give a digested sample; a mixture of standard peptide fragments and isotope-labeled peptide fragments with the same concentration of digested peptide fragments as that in the digested sample is formulated as a standard solution, and the concentration of the digested peptide fragments in the digested sample is tested using the following method;

the digested sample and the standard solution are analyzed by HPLC-tandem mass spectrometry using an aqueous solution containing 0.1% formic acid as mobile phase A and an acetonitrile solution containing 0.1% formic acid as mobile phase B; the injection volume is 3 to 20 μL, and a 2.1 mm×150 mm C18 reversed-phase chromatography column is used for isolation at a flow rate of 0.2 mL/min, the gradient of mobile phase changes linearly from 100% mobile phase A to 100% mobile phase B to achieve the isolation of the digested peptide fragments; a triple tandem quadrupole mass spectrometer is used for detection to harvest mass spectrometry signals from various standard peptide fragments and corresponding isotope-labeled peptide fragments, and each of the digested samples and the standard solutions are analyzed in triplicate, the concentrations of various standard peptide fragments in the digested samples are calculated according to the concentrations of the standard peptide fragments and the isotope-labeled peptide fragments in the standard solution and their mass respectively added, as well as the peak areas of the standard peptide fragments and isotope-labeled peptide fragments in the extraction chromatogram of the digested samples, the peak areas of the standard peptide fragments and isotope-labeled peptide fragments in the extraction chromatogram of the standard solution, the sample mass, and the concentration and mass of the isotope-labeled peptide fragments added in the sample, and the concentration of N protein in the sample is calculated according to the molecular weight of the standard peptide fragments and N protein according to the formulas below:

$$R_{STD} = \frac{c_{pep} M_{pep}}{c'_{pep} M'_{pep}}$$

$$c_s = \frac{R_{STD} A_s c'_s M'_s}{A_{STD} M_s}$$

$$c_N = \frac{c_s}{\mathrm{MW}_s} \times \mathrm{MW}_N$$

in the formula, $R_{STD}$ is a ratio of the mass of the standard peptide fragment to the mass of the isotope-labeled peptide fragment in the standard solution, $c_{pep}$ is a concentration of the standard peptide fragment, $M_{pep}$ is a mass of the standard peptide fragment added, $c'_{pep}$ is a concentration of the isotope-labeled peptide fragment, $M'_{pep}$ is a mass of the isotope-labeled peptide fragment added, $c_s$ is a concentration of the standard peptide fragment in the digested sample, $A_s$ is a ratio of peak area of the standard peptide fragment to the isotope-labeled peptide fragment in the sample, $c'_s$ is a concentration of the isotope-labeled peptide fragment added in the sample, $M'_s$ is a mass of the isotope-labeled peptide fragment added in the sample, $A_{STD}$ is a ratio of peak area of the standard peptide fragment to the isotope-labeled peptide fragment in the standard solution, $M_s$ is a sample mass, $c_N$ is a concentration of N protein in the sample, $MW_s$ is a molecular weight of the standard peptide fragment, and $MW_N$ is a molecular weight of the N protein;

the obtained measurement results are tested according to the K-S single-sample normality test and the Grabs method and/or Dixon method are used for outlier test; for samples that pass the statistical test, the arithmetic mean value of all the results is taken as the standard value of test results of peptide fragment analysis-based HPLC-IDMS; while for samples that fail to pass the statistical K-S single-sample normality test, Grabs method and/or Dixon method for outlier test, the number of samples is increased and the step (o) is repeated until passed;

(VI). determination and statistical test of standard value of nCOV N protein reference material the at least 15 data of N protein content obtained by the amino acid analysis-based HPLC-IDMS in step (n) and the at least 15 data of N protein content obtained by the peptide fragment analysis-based HPLC-IDMS in step (o) are subject to independent-samples t-test; if the |t| value calculated from Formula 24 is less than $t_{\alpha,(n_1+n_2-2)}$, wherein $t_{\alpha,(n_1+n_2-2)}$ is obtained by look-up in GB/T 4086.3-1983, the Tables for statistical distributions—t-distribution, then it is considered that the t-test result is passed, indicating that there is no systematic bias between the certified results of the two methods; the arithmetic mean value of the two methods is taken as a certified value x, and when the t-test result fails, the step (V) is repeated;

$$t = \frac{\overline{X_1} - \overline{X_2}}{\sqrt{\frac{s_1^2}{n_1} + \frac{s_2^2}{n_2}}} \quad \text{Formula 24}$$

in Formula 24:

$\overline{X_1}$—mean number of the first sample, that is, a standard value of the test results by the amino acid analysis-based HPLC-IDMS;

$\overline{X_2}$—mean number of the second sample, that is, a standard value of the test results by the peptide fragment analysis-based HPLC-IDMS;

$s_1^2$—variance of the first sample, $$s_1^2 = \frac{\sum_{i=1}^{n_1} (X_i - \overline{X_1})^2}{n_1 - 1};$$

$s_2^2$—variance of the second sample, $$s_2^2 = \frac{\sum_{j=1}^{n_2} (X_j - \overline{X_2})^2}{n_2 - 1};$$

$n_1$—volume of the first sample, that is, a number determined by the amino acid analysis-based HPLC-IDMS;

$n_2$—volume of the second sample, that is, a number determined by the peptide fragment analysis-based HPLC-IDMS;

(VII). assessment of uncertainty of the certified results of the standard value of the nCOV N protein reference material the uncertainty U of the certified results of the nCOV N protein reference material is derived from an uncertainty $u_{char}$ introduced during the certification, an uncertainty $u_{bb}$ introduced by the uniformity of reference material, an uncertainty $u_{sts}$ introduced by short-term stability and an uncertainty $u_{lts}$ introduced by long-term stability, which are combined according to Formula 25

$$U = k'\sqrt{u_{char}^2 + u_{bb}^2 + u_{lts}^2 + u_{sts}^2} \quad \text{Formula 25}$$

in the formula, k'is a coverage factor, typically k'=2;

wherein, $u_{char}$ comprises an uncertainty $u_{char,HPLC\text{-}AAA\text{-}IDMS}$ from the amino acid analysis-based HPLC-IDMS and an uncertainty $u_{char,HPLC\text{-}PEP\text{-}IDMS}$ from the peptide fragment analysis-based HPLC-IDMS; and $u_{char,HPLC\text{-}AAA\text{-}IDMS}$ comprises an uncertainty component $u_{char,HPLC\text{-}AAA\text{-}IDMS,A}$ Formula 26 introduced by the repeatability of the test results of the amino acid analysis-based HPLC-IDMS, as well as an uncertainty component $u_{char,HPLC\text{-}AAA\text{-}IDMS,wi}$ Formula 27 introduced by multiple balance weighing, and an uncertainty component $u_{char,HPLC\text{-}AAA\text{-}IDMS,P}$ Formula 28 introduced by the amino acid reference material, which are combined according to Formula 29, $$u_{char,HPLC-AAA-IDMS,A} = \frac{s}{\sqrt{n}} \quad \text{Formula 26}$$

in Formula 26, s is a standard deviation, i.e., $$s = \sqrt{\frac{\sum_{i=1}^{n} (x_i - \overline{x})^2}{n - 1}},$$

$x_i - \overline{x}$ is a deviation between a certain data and the sample mean, and n is number of measurements;

$$u_{char,HPLC-AAA-IDMS,wi} = \frac{|MPE|}{\sqrt{3}} \quad \text{Formula 27}$$

in Formula 27, MPE is a maximum permissible error of balance verification certificate $$u_{char,HPLC-AAA-IDMS,P} = \frac{U}{k'} \quad \text{Formula 28}$$

in Formula 28, U is an uncertainty in the certificate of national amino acid reference material, k' is a coverage factor, typically k'=2;

$$u_{char,HPLC-AAA-IDMS} = \sqrt{u^2_{char,HPLC-AAA-IDMS,A} + \sum_{i=1}^{q} (c_i u_{char,HPLC-AAA-IDMS,wi})^2 + c_p^2 u^2_{char,HPLC-AAA-IDMS,p}} \quad \text{Formula 29}$$

in Formula 29, q is a number of balance weighing, $c_i$ is a sensitivity coefficient at the $i^{th}$ weighing, and $c_p$ is a sensitivity coefficient of the purity of the reference material which is calculated according to JJF1059.1-2012, the Evaluation and Expression of Uncertainty in Measurement;

$u_{char,HPLC\text{-}PEP\text{-}IDMS}$ comprises an uncertainty component $u_{char,HPLC\text{-}PEP\text{-}IDMS,A}$ Formula 30 introduced by the repeatability of the test results of the amino acid analysis-based HPLC-IDMS, as well as an uncertainty component $u_{char,HPLC\text{-}PEP\text{-}IDMS,wi}$ Formula 31 introduced by multiple balance weighing, and an uncertainty component $u_{char,HPLC\text{-}PEP\text{-}IDMS,P}$ Formula 32 introduced by the peptide fragment reference material, which are combined according to Formula 33, $$u_{char,HPLC-pep-IDMS,A} = \frac{s}{\sqrt{n}} \quad \text{Formula 30}$$

in Formula 30, s is a standard deviation, i.e., $$s = \sqrt{\frac{\sum_{i=1}^{n}(x_i - \bar{x})^2}{n-1}},$$

$x_i - \bar{x}$ is a deviation between a certain data and the sample mean, and n is number of measurements;

$$u_{char,HPLC-pep-IDMS,wi} = \frac{|MPE|}{\sqrt{3}} \quad \text{Formula 31}$$

in Formula 31, MPE is the maximum permissible error of balance verification certificate $$u_{char,HPLC-pep-IDMS,P} = \frac{U}{k'} \quad \text{Formula 32}$$

$$u_{char,HPLC-PEP-IDMS} = \sqrt{u^2_{char,HPLC-PEP-IDMS,A} + \sum_{i=1}^{q}(c_i u_{char,HPLC-PEP-IDMS,wi})^2 + c_p^2 u^2_{char,HPLC-PEP-IDMS,p}} \quad \text{Formula 33}$$

in Formula 33, q is a number of balance weighing, $c_i$ is a sensitivity coefficient at the $i^{th}$ weighing, and $c_p$ is a sensitivity coefficient of the purity of the reference material;

$u_{char}$ is calculated according to Formula 34:

$$u_{char} = \frac{1}{2}\sqrt{u^2_{char,HPLC-AAA-IDMS} + u^2_{char,\ HPLC-PEP-IDMS}} \quad \text{Formula 34}$$

when mean square between groups is greater than or equal to mean square within group, the uncertainty introduced by uniformity is calculated according to Formula 35;

$$u_{bb} = S_{bb} = \sqrt{\frac{1}{n}\left(\frac{Q_1}{v_1} - \frac{Q_2}{v_2}\right)} = \sqrt{\frac{s_1^2 - s_2^2}{n}} \quad \text{Formula 35}$$

when the mean square between groups is less than the mean square within group, the uncertainty introduced by uniformity is calculated according to Formula 36;

$$u_{bb} = S_{bb} = \sqrt{\frac{s_2^2}{n}}\sqrt[4]{\frac{2}{v_2}} \quad \text{Formula 36}$$

the uncertainty introduced by short-term stability and the uncertainty introduced by long-term stability of the reference material are calculated according to Formula 37 and Formula 38:

$$u_{sts} = s_{k,sts} \cdot t_{sts} \quad \text{Formula 37}$$

-continued $$u_{lts} = s_{k,lts} \cdot t_{lts} \quad \text{Formula 38}$$

in the formulas, the $s_{k,sts}$ is s(b) in the short-term stability test obtained from Formula 19, and $t_{ts}$ is the duration in the short-term stability test, in day;

the $s_{k,lts}$ is s(b) in the long-term stability test obtained from Formula 23, and $t_{lts}$ is the duration in the long-term stability test, in month;

the above results are combined according to Formula 25 to give an expanded uncertainty U of the certified value of the reference material, so that the certified result of the nCOV N protein reference material can be represented as:

$$x \pm U$$

in the formula, x is the certified value, and U is the expanded uncertainty of the certified value;

and finally, certified results of the uniformity, stability, and N protein content of the prepared nCOV N protein reference material are obtained.

2. The method for preparing and certifying a novel coronavirus nucleocapsid protein (nCOV N protein) of claim 1, wherein, in step (a), the biochemical reagent is purified by an isoelectric focusing electrophoresis instrument in which 0.01 to 1 mol/L of phosphoric acid and 0.01 to 1 mol/L of sodium hydroxide are used as electrophoresis solution at two ends of the isoelectric focusing electrophoresis instrument, respectively; after completion of the isoelectric focusing, fractions with isoelectric point around 10.5 are collected, and the biochemical reagent is then purified over a molecular sieve column, the appearance time of peak is monitored at an absorbance of 280 nm to collect the fractions during the period of the appearance time, the collected fractions are repeatedly purified over the molecular sieve column; after repeating the purification over the molecular sieve column three times, the fraction obtained at the last appearance time of peak is collected to complete the purification of the nCOV N protein.

3. The method for preparing and certifying a novel coronavirus nucleocapsid protein (nCOV N protein) of claim 2, wherein, in step (b), the number of the isotope-labeled atoms is not less than 3.

4. The method for preparing and certifying a novel coronavirus nucleocapsid protein (nCOV N protein) of claim 3, wherein, in step (f), the universal protein purity analysis method comprises: reversed HPLC, and/or ion exchange chromatography HPLC, and/or gel exclusion HPLC, and/or hydrophobic interaction HPLC, and/or immunoaffinity HPLC, which, co-operating with UV, and/or fluorescence, and/or differential refraction, and/or evaporative light scattering, and/or fluorescence electrospray ionization, and/or circular dichroism spectrometer, is used to characterize the purity of the reference material.

5. The method for preparing and certifying a novel coronavirus nucleocapsid protein (nCOV N protein) of claim 3, wherein, in step (f), the universal protein purity analysis method further comprises SDS-PAGE gel electrophoresis, and/or capillary electrophoresis, and/or chip electrophoresis, and/or two-dimensional electrophoresis, which, co-operating with UV and/or fluorescence, is used to characterize the purity of the reference material.

6. The method for preparing and certifying a novel coronavirus nucleocapsid protein (nCOV N protein) of claim 3, wherein, in step (f), the universal protein purity analysis method further comprises high performance liquid chromatography-mass spectrometry (HPLC-MS), and/or matrix-assisted laser-induced desorption time-of-flight mass spectrometry, which is used to characterize the purity of the reference material.

7. The method for preparing and certifying a novel coronavirus nucleocapsid protein (nCOV N protein) of claim 3, wherein, in step (f), the universal protein purity analysis method further comprises electrochemical method or nuclear magnetic resonance spectroscopy, which is used to characterize the purity of the reference material.

8. The method for preparing and certifying a novel coronavirus nucleocapsid protein (nCOV N protein) of claim 1, wherein, in step (0), in the test with the triple tandem quadrupole mass spectrometer, a positive ion mode and a selective ion monitoring (SIM) or multiple reaction monitoring (MRM) scanning mode are used.

* * * * *

SEQUENCE LISTING

```
Sequence total quantity: 26
SEQ ID NO: 1              moltype = AA  length = 419
FEATURE                   Location/Qualifiers
source                    1..419
                          mol_type = protein
                          organism = unidentified
SEQUENCE: 1
MSDNGPQNQR NAPRITFGGP SDSTGSNQNG ERSGARSKQR RPQGLPNNTA SWFTALTQHG  60
KEDLKFPRGQ GVPINTNSSP DDQIGYYRRA TRRIRGGDGK MKDLSPRWYF YYLGTGPEAG  120
LPYGANKDGI IWVATEGALN TPKDHIGTRN PANNAAIVLQ LPQGTTLPKG FYAEGSRGGS  180
QASSRSSSRS RNSSRNSTPG SSRGTSPARM AGNGGDAALA LLLLDRLNQL ESKMSGKGQQ  240
QQGQTVTKKS AAEASKKPRQ KRTATKAYNV TQAFGRRGPE QTQGNFGDQE LIRQGTDYKH  300
WPQIAQFAPS ASAFFGMSRI GMEVTPSGTW LTYTGAIKLD DKDPNFKDQV ILLNKHIDAY  360
KTFPPTEPKK DKKKKADETQ ALPQRQKKQQ TVTLLPAADL DDFSKQLQQS MSSADSTQA   419

SEQ ID NO: 2              moltype = AA  length = 10
FEATURE                   Location/Qualifiers
source                    1..10
                          mol_type = protein
                          organism = synthetic construct
SEQUENCE: 2
MSDNGPQNQR                                                         10

SEQ ID NO: 3              moltype = AA  length = 18
FEATURE                   Location/Qualifiers
source                    1..18
                          mol_type = protein
                          organism = synthetic construct
SEQUENCE: 3
ITFGGPSDST GSNQNGER                                                18

SEQ ID NO: 4              moltype = AA  length = 20
FEATURE                   Location/Qualifiers
source                    1..20
                          mol_type = protein
                          organism = synthetic construct
SEQUENCE: 4
PQGLPNNTAS WFTALTQHGK                                              20

SEQ ID NO: 5              moltype = AA  length = 20
FEATURE                   Location/Qualifiers
source                    1..20
                          mol_type = protein
                          organism = synthetic construct
SEQUENCE: 5
GQGVPINTNS SPDDQIGYYR                                              20

SEQ ID NO: 6              moltype = AA  length = 20
FEATURE                   Location/Qualifiers
source                    1..20
                          mol_type = protein
                          organism = synthetic construct
SEQUENCE: 6
WYFYYLGTGP EAGLPYGANK                                              20

SEQ ID NO: 7              moltype = AA  length = 16
FEATURE                   Location/Qualifiers
source                    1..16
                          mol_type = protein
                          organism = synthetic construct
SEQUENCE: 7
```

```
DGIIWVATEG ALNTPK                                            16

SEQ ID NO: 8          moltype = AA  length = 20
FEATURE               Location/Qualifiers
source                1..20
                      mol_type = protein
                      organism = synthetic construct
SEQUENCE: 8
NPANNAAIVL QLPQGTTLPK                                        20

SEQ ID NO: 9          moltype = AA  length = 8
FEATURE               Location/Qualifiers
source                1..8
                      mol_type = protein
                      organism = synthetic construct
SEQUENCE: 9
GFYAEGSR                                                     8

SEQ ID NO: 10         moltype = AA  length = 8
FEATURE               Location/Qualifiers
source                1..8
                      mol_type = protein
                      organism = synthetic construct
SEQUENCE: 10
GGSQASSR                                                     8

SEQ ID NO: 11         moltype = AA  length = 8
FEATURE               Location/Qualifiers
source                1..8
                      mol_type = protein
                      organism = synthetic construct
SEQUENCE: 11
NSTPGSSR                                                     8

SEQ ID NO: 12         moltype = AA  length = 17
FEATURE               Location/Qualifiers
source                1..17
                      mol_type = protein
                      organism = synthetic construct
SEQUENCE: 12
MAGNGGDAAL ALLLLDR                                           17

SEQ ID NO: 13         moltype = AA  length = 7
FEATURE               Location/Qualifiers
source                1..7
                      mol_type = protein
                      organism = synthetic construct
SEQUENCE: 13
LNQLESK                                                      7

SEQ ID NO: 14         moltype = AA  length = 11
FEATURE               Location/Qualifiers
source                1..11
                      mol_type = protein
                      organism = synthetic construct
SEQUENCE: 14
GQQQQGQTVT K                                                 11

SEQ ID NO: 15         moltype = AA  length = 7
FEATURE               Location/Qualifiers
source                1..7
                      mol_type = protein
                      organism = synthetic construct
SEQUENCE: 15
SAAEASK                                                      7

SEQ ID NO: 16         moltype = AA  length = 10
FEATURE               Location/Qualifiers
source                1..10
                      mol_type = protein
                      organism = synthetic construct
SEQUENCE: 16
AYNVTQAFGR                                                   10

SEQ ID NO: 17         moltype = AA  length = 16
FEATURE               Location/Qualifiers
source                1..16
                      mol_type = protein
                      organism = synthetic construct
```

-continued

```
SEQUENCE: 17
GPEQTQGNFG DQELIR                                                 16

SEQ ID NO: 18          moltype = AA  length = 6
FEATURE                Location/Qualifiers
source                 1..6
                       mol_type = protein
                       organism = synthetic construct
SEQUENCE: 18
QGTDYK                                                            6

SEQ ID NO: 19          moltype = AA  length = 20
FEATURE                Location/Qualifiers
source                 1..20
                       mol_type = protein
                       organism = synthetic construct
SEQUENCE: 19
HWPQIAQFAP SASAFFGMSR                                             20

SEQ ID NO: 20          moltype = AA  length = 19
FEATURE                Location/Qualifiers
source                 1..19
                       mol_type = protein
                       organism = synthetic construct
SEQUENCE: 20
IGMEVTPSGT WLTYTGAIK                                              19

SEQ ID NO: 21          moltype = AA  length = 8
FEATURE                Location/Qualifiers
source                 1..8
                       mol_type = protein
                       organism = synthetic construct
SEQUENCE: 21
DQVILLNK                                                          8

SEQ ID NO: 22          moltype = AA  length = 6
FEATURE                Location/Qualifiers
source                 1..6
                       mol_type = protein
                       organism = synthetic construct
SEQUENCE: 22
HIDAYK                                                            6

SEQ ID NO: 23          moltype = AA  length = 8
FEATURE                Location/Qualifiers
source                 1..8
                       mol_type = protein
                       organism = synthetic construct
SEQUENCE: 23
TFPPTEPK                                                          8

SEQ ID NO: 24          moltype = AA  length = 10
FEATURE                Location/Qualifiers
source                 1..10
                       mol_type = protein
                       organism = synthetic construct
SEQUENCE: 24
ADETQALPQR                                                        10

SEQ ID NO: 25          moltype = AA  length = 17
FEATURE                Location/Qualifiers
source                 1..17
                       mol_type = protein
                       organism = synthetic construct
SEQUENCE: 25
QQTVTLLPAA DLDDFSK                                                17

SEQ ID NO: 26          moltype = AA  length = 14
FEATURE                Location/Qualifiers
source                 1..14
                       mol_type = protein
                       organism = synthetic construct
SEQUENCE: 26
QLQQSMSSAD STQA                                                   14
```